(12) United States Patent
Ogura et al.

(10) Patent No.: US 7,693,334 B2
(45) Date of Patent: Apr. 6, 2010

(54) PATHOLOGICAL DIAGNOSIS SUPPORT DEVICE, PROGRAM, METHOD, AND SYSTEM

(75) Inventors: Maki Ogura, Tokyo (JP); Akira Saitou, Tokyo (JP); Kenichi Kamijo, Tokyo (JP); Kenji Okajima, Tokyo (JP); Tomoharu Kiyuna, Tokyo (JP)

(73) Assignee: NEC Corporation, Tokyo (JP)

( * ) Notice: Subject to any disclaimer, the term of this patent is extended or adjusted under 35 U.S.C. 154(b) by 1162 days.

(21) Appl. No.: 11/290,294

(22) Filed: Nov. 30, 2005

(65) Prior Publication Data
US 2006/0115146 A1 Jun. 1, 2006

(30) Foreign Application Priority Data
Nov. 30, 2004 (JP) ............................. 2004-346911

(51) Int. Cl.
- *G06K 9/46* (2006.01)
- *G06K 9/66* (2006.01)
- *G06K 9/50* (2006.01)
- *G06K 9/00* (2006.01)

(52) U.S. Cl. ..................... 382/190; 382/201; 382/128

(58) Field of Classification Search ......... 382/128–133, 382/143, 159, 224, 190–208
See application file for complete search history.

(56) References Cited

U.S. PATENT DOCUMENTS

| | | | |
|---|---|---|---|
| 6,603,873 B1 * | 8/2003 | Gordon et al. | 382/144 |
| 2003/0156273 A1 * | 8/2003 | Kageyama et al. | 356/52 |
| 2004/0017509 A1 * | 1/2004 | Kondo et al. | 348/453 |
| 2005/0169516 A1 * | 8/2005 | Okajima et al. | 382/159 |
| 2005/0197864 A1 * | 9/2005 | Koritzinsky et al. | 705/2 |
| 2006/0247514 A1 * | 11/2006 | Panasyuk et al. | 600/410 |
| 2008/0167068 A1 * | 7/2008 | Mosleh et al. | 455/553.1 |

FOREIGN PATENT DOCUMENTS

EP 1 480 167 A1 11/2004

(Continued)

OTHER PUBLICATIONS

Petushi S. et al., "Automated Identification of Microstructures on Histology Slides", *Biomedical Imaging: Macro to Nano*, pp. 424-427 (2004), XP010773888.

(Continued)

*Primary Examiner*—Wesley Tucker
*Assistant Examiner*—Randolph Chu
(74) *Attorney, Agent, or Firm*—Scully, Scott, Murphy & Presser, P.C.

(57) ABSTRACT

A pathological diagnosis support device, a pathological diagnosis support program, a pathological diagnosis support method, and a pathological diagnosis support system extract a pathological tissue for diagnosis from a pathological image and diagnose the pathological tissue. A tissue collected in a pathological inspection is stained using, for example, hematoxylin and eosin. In consideration of the state of the tissue in which a cell nucleus and its peripheral constituent items are stained in respective colors unique thereto, subimages such as a cell nucleus, a pore, cytoplasm, interstitium are extracted from the pathological image, and color information of the cell nucleus is also extracted. The subimages and the color information are stored as feature candidates so that presence or absence of a tumor and benignity or malignity of the tumor are determined.

40 Claims, 14 Drawing Sheets

FOREIGN PATENT DOCUMENTS

| | | |
|---|---|---|
| JP | HEI 10-197522 | 7/1998 |
| JP | 2001-101418 A | 4/2001 |
| JP | 2003-256839 | 9/2003 |
| WO | WO 95/22114 | 8/1995 |
| WO | WO03073381 * | 9/2003 |
| WO | 2004/025569 A2 | 3/2004 |
| WO | WO 2004/072900 | 8/2004 |

OTHER PUBLICATIONS

Teverovskiy M. et al., "Improved Prediction of Prostate Cancer Recurrence Based on an Automated Tissue Image Analysis System", *Biomedical Imaging: Macro to Nano*, pp. 257-260 (2004), XP010773846.

Anonymous: "LifeSpan BioSciences and NEC Announce Partnership to Develop Cancer Diagnosis Support System", *Internet Citation. Business Wire Press Release*, p. 1 (2003), XP002368114.

Mouroutis et al.; "Compact Hough Transform and a Maximum Likelihood Approach to Cell Nuclei Detection," Digital Signal Processing Proceedings, 1997, 13th International Conference on Santorini, Greece Jul. 2-4, 1997, New York, NY, USA, IEEE, US, vol. 2, Jul. 2, 1997 pp. 869-872.

Gonzalez, R. C. et al.; Digital Image Processing, Upper Saddle River, NJ; Prentice Hall, US, 2002, XP 002391293, The Convolution and Correlation Theorems pp. 205-208, "Segmentation in RGB Vector Space" pp. 333-335.

Smolka, B. et al.; "Towards Automatic Redeye Effect Removal," Pattern Recognition Letters, North-Holland Publication Amsterdam, NL, vol. 24, No. 11, Jul. 2003 pp. 1767-1785.

Seul, M. et al.; "Practical Alogorithms for Image Analysis, Passage" Cambridge University Press, 2001, XP 002391303 Template Matching pp. 106-109.

Akira Saito, et al., "Computer Assisted Cancer Diagnosis", NEC Technical Report, vol. 56, No. 10, pp. 52-56: published Nov. 25, 2003.

* cited by examiner

F I G. 1
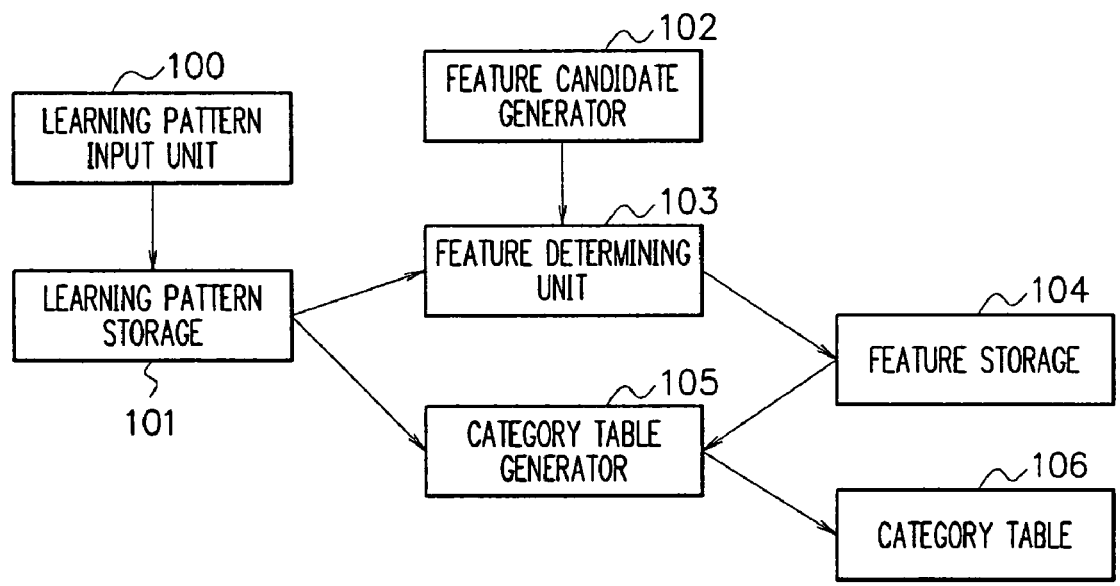

| q | $C_1$ | $C_2$ | $C_3$ | $C_4$ | $C_5$ | | $C_{n-1}$ | $C_n$ |
|---|---|---|---|---|---|---|---|---|
| 1 | 1 | 1 | 0 | * | * | | * | * |
| 1 | 1 | 0 | 1 | 1 | 1 | | 1 | 1 |
| 0 | 0 | 0 | 0 | 1 | * | | * | * |
| 0 | 0 | 0 | 1 | 0 | 0 | | 0 | 0 |
| 1 | 1 | 0 | 1 | 0 | 1 | | 0 | 1 |
| 0 | 1 | 1 | 1 | * | * | | * | * |
| 0 | 0 | 0 | 0 | 1 | 0 | | 0 | * |

| m \ i | 1 C1=1 | C1=0 | 2 C1=1 | C1=0 | 3 C1=1 | C1=0 | ... | n Cn=1 | Cn=0 | i |
|---|---|---|---|---|---|---|---|---|---|---|
| | 30 | 34 | – | – | – | – | | 1 | 1 | 1 |
| | 30 | 34 | – | – | – | – | | 1 | 2 | 2 |
| | 30 | 34 | – | – | – | – | | 2 | 4 | 3 |
| | 30 | 34 | – | – | – | – | | 23 | 26 | 25 |
| | 30 | 34 | – | – | – | – | | 24 | 27 | 26 |
| | 30 | 34 | – | – | – | – | | 25 | 28 | 27 |
| | 30 | 34 | – | – | 25 | 30 | | 26 | 29 | 28 |
| | 30 | 34 | – | – | – | – | | 27 | 30 | 29 |
| | 30 | 34 | 28 | 31 | – | – | | 28 | 31 | 30 |
| | 30 | 34 | – | – | 28 | 33 | | 29 | 32 | 31 |
| | 30 | 34 | – | – | 29 | 34 | | 29 | 33 | 32 |
| | 30 | 34 | – | – | – | – | | 30 | 34 | 33 |
| | 30 | 34 | 32 | 36 | – | – | | 32 | 33 | 34 |
| | 30 | 34 | – | – | – | – | | 33 | 35 | 35 |
| | 30 | 34 | – | – | 33 | 38 | | 34 | 36 | 36 |
| | 30 | 34 | – | – | – | – | | 35 | 38 | 37 |
| | 30 | 34 | – | – | – | – | | 35 | 40 | 38 |
| | 30 | 34 | – | – | – | – | | 37 | 41 | 39 |
| | 30 | 34 | – | – | – | – | | 62 | 64 | 63 |
| | 30 | 34 | – | – | – | – | | 64 | 64 | 64 |

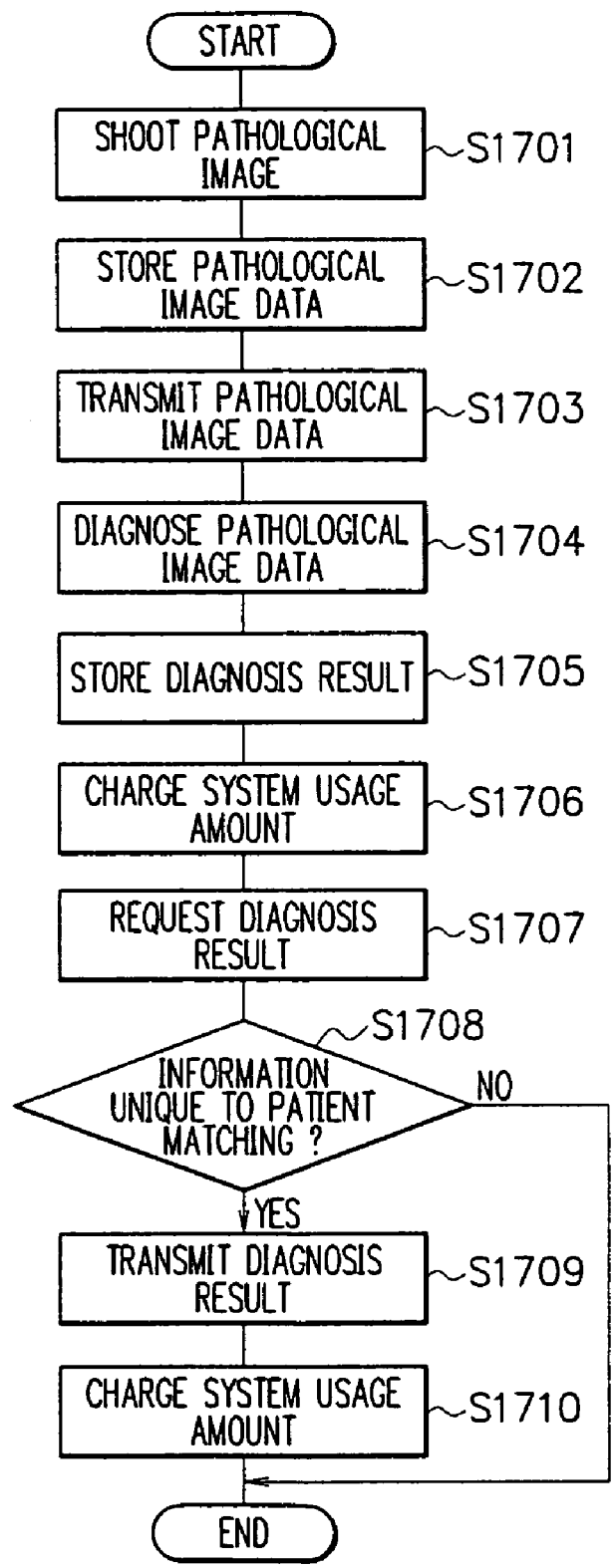

PATHOLOGICAL DIAGNOSIS SUPPORT DEVICE, PROGRAM, METHOD, AND SYSTEM

BACKGROUND OF THE INVENTION

1. Field of the Invention

The present invention relates to a pathological diagnosis support device, and in particular, to a pathological diagnosis support device, pathological diagnosis support program, pathological diagnosis support method, and pathological diagnosis support system in which a pathological tissue to be diagnosed is extracted from a pathological image for diagnosis thereof.

2. Description of the Prior Art

In a clinical site, subtle extraordinary events can be detected thanks to development of diagnosis support devices using images such as images produced by x-ray photography, computer tomography (CT), and magnetic resonance imaging (MRI). However, since the devices produce only positional information of foreign substances, properties of the foreign substances cannot be identified. In consequence, a pathological expert observes by a microscope the foreign substances detected by the diagnosis device and determines malignity or benignity of the substance according to her or his phathological experiences. Therefore, for an example of the diagnosis in a vague boundary zone, the diagnostic result varies between the pathologists.

Specifically, in a pathological inspection, a tissue collected from an organ is dehydrated to be fixed using paraffin through a blocking process. The block is sliced into sections each having a thickness of five microns to eight microns, and then paraffin is removed from the sections. The section is stained to be observed by a microscope. The pathologist checks an image created by the microscope to diagnose the foreign substance on the basis of morphological information such as changes in size and shape of cellular nuclei and changes in patterns as tissues.

Japanese Patent Application Laid-Open No. 10-197522 describes a pathological tissue diagnosis support device in which a feature of an image obtained from a tissue image of a tissue of an organ is quantitatively represented as a feature quantity. Diagnosis categories beforehand set according to a pathological histological feature are employed as similarity calculation categories to calculate degrees of similarity of the feature quantity of the tissue image with respect to the similarity calculation categories. Resultantly, names of similarity calculation categories having a high degree of similarity are displayed.

Japanese Patent Application Laid-Open No. 2001-101418 proposes a feature extraction device in which a learning pattern as a discrimination object is projected onto a group of subspaces, and a square of length of the projection of the learning pattern onto each subspace is calculated as a feature vector. The device updates basic vectors of each subspace of the subspace group to increase a ratio between an inter-class variation and an intra-class variation of each element of the feature vector. As a result, the feature extraction device is stable against pattern variations and is suitable to discriminate patterns.

Japanese Patent Application Laid-Open No. 2003-256839 describes a pattern feature selection method, a pattern feature classification method, a pattern feature determination method, a program for the pattern feature selection, classification, and determination, and a device for the pattern feature selection, classification, and determination to implement high-performance pattern discrimination without requiring quite a large amount of learning.

NEC Technical Report Vol. 56, No. 10 published on Nov. 25, 2003 describes an automatic cancer cell extraction technique in which using pathological images, patterns of constituent elements of tissues such as a gland and interstitium, i.e., a connective tissue of glands are learned for detection thereof. As a result, it is possible to determine malignity of cancer with high accuracy.

However, the above inventions are attended with problems as follows.

According to the device described in Japanese Patent Application Laid-Open No. 10-197522, a neural network is adopted to calculate the similarity. That is, the similarity can be automatically calculated with high accuracy through a learning process only by preparing learning data. The learning data increases as the number of samples used by the device becomes greater. This improves the accuracy in the calculation of similarity. However, since the operation requires a considerably large volume of learning data, a long period of time is consumed to produce the similarity with high reliability.

In the methods of extracting patterns described in Japanese Patent Application Laid-Open Nos. 10-197522, 2001-101418, and 2003-256839 and NEC Technical Report Vol. 56, No. 10, it is possible to detect a feature, e.g., a tumor in the image obtained from the texture image of a living body. However, since particular situations inherent to the pathological image are not taken into consideration in the extraction of the feature from the pathological image, the part of the image indicating the feature cannot be detected with high precision.

SUMMARY OF THE INVENTION

It is therefore an object of the present invention to provide a pathological diagnosis support device, pathological diagnosis support program, pathological diagnosis support method, and pathological diagnosis support system in which by giving consideration to importance of changes of a cell nucleus, peripheral tissues thereof, and the like in the discrimination of properties of a tumor, subimages primarily including cell nuclei, pores, cytoplasm, and interstitium are extracted from a pathological image. The subimages are received as input items such as learning patterns and input patterns. According to the subimages, presence or absence of a tumor and benignity or malignity thereof can be determined with high accuracy.

Another object of the present invention is to provide a pathological diagnosis support device, pathological diagnosis support program, pathological diagnosis support method, and pathological diagnosis support system in which by taking into consideration a situation that a tissue collected for pathological inspection is stained using, for example, hematoxylin and eosin and hence cell nuclei and peripheral tissues thereof are stained in particular colors, when subimages primarily including cell nuclei, pores, cytoplasm, and interstitium are extracted from a pathological image, color information of the cell nuclei is simultaneously obtained therefrom to store the subimages and the color information as feature candidates. As a result, presence or absence of a tumor and benignity or malignity thereof can be determined with high accuracy.

In accordance with a first aspect of the present invention, there is provided a pathological diagnosis support device, including a learning pattern input unit for obtaining from a pathological image to be used for learning, images centered on a tumor and inputting thereto the images as learning patterns; a learning pattern storage unit for storing and keeping the learning patterns to which class information is attached; a feature candidate generator unit for generating a plurality of feature candidates; a feature determining unit for determining a feature set of features suitable for diagnosis using the feature candidates generated by the feature candidate generator unit; a feature storage unit for storing and keeping the set of features determined by the feature determining unit; a category table generator unit for generating a category table; a pattern input unit for obtaining, from a pathological image to be diagnosed, images centered on a tumor candidate and inputting the images as input patterns; a feature extracting unit for extracting features from the input patterns; and a diagnosis unit for conducting diagnosis using the features. The feature determining unit calculates a feature of each of the learning patterns corresponding to each of the feature candidates and determines as a first feature of the feature set, a feature candidate for which a mutual information quantity with respect to the class information of a set of the learning patterns takes a maximum value; and sequentially determines, under a condition that the determined feature is known, as a subsequent feature of the feature set, a feature candidate for which mutual information quantity between a feature of each learning pattern corresponding to each feature candidate and the class information of an associated one of the learning patterns takes a maximum value. The category table generator unit calculates each feature of each of the learning patterns using the feature set and classifies the patterns using the category table including each feature of the learning patterns and the class information. The feature extracting unit calculates each feature of the input patterns using the feature set.

In accordance with a second aspect of the present invention, the diagnosis unit diagnoses the input patterns according a result of the diagnosis and the category table.

In accordance with a third aspect of the present invention, the feature determining means prepares a predetermined number of sets for a transition of the learning pattern according to a value of the feature, calculates the feature of each of the learning patterns, determines the feature candidate, distributes the learning pattern with a weight according to the feature thus determined, sequentially causes a transition of the learning pattern to one of the sets corresponding to the feature, and sequentially determines the feature candidate under a condition that information about the sets respectively containing the learning patterns and the determined feature are known; and the diagnosis means causes a transition of each of the input patterns according to each feature of the input patterns and a transition table sequentially having recorded a set to which the learning pattern belongs at determination of each feature of the feature set and diagnoses the input patterns according a set to which the input pattern belongs as a result of the transition.

In accordance with a fourth aspect of the present invention, the feature determining means prepares a predetermined number of sets for a transition of the learning pattern according to a value of the feature, calculates the feature of each of the learning patterns, determines the feature candidate, distributes the learning pattern with a weight according to the feature thus determined, sequentially causes a transition of the learning pattern to one of the sets corresponding to the feature, and sequentially determines the feature candidate under a condition that information about the sets respectively containing the learning patterns and the determined feature are known, the feature extracting means calculates the feature that indicates a probability with which the feature at an order takes a predetermined value, and the diagnosis means calculates, according to each feature of the input patterns and a transition table sequentially having recorded a set to which the learning pattern belongs at determination of each feature of the feature set, a probability with which the input pattern includes predetermined class information and then conducts the diagnosis.

In accordance with a fifth aspect of the present invention, the learning pattern input unit and the pattern input unit select, from R, G, and B values of each pixel in the pathological image stained in advance, pixels belonging to a color region to which a cell nucleus of a predetermined tumor belongs, calculate distance between a center of distribution of the color region and each pixel belonging to the color region, assign a signal to the pixel according to the distance, detect a peak of distribution of the signals in the pathological image, and input an image centered on the peak as the learning pattern.

In accordance with a sixth aspect of the present invention, the feature candidates generated by the feature generator unit includes a feature candidate obtained using a complex Gabor function as a feature extraction function.

In accordance with a seventh aspect of the present invention, the feature candidates generated by the feature generator unit includes a feature candidate obtained using a feature extraction function obtained by normalizing a complex Gabor function and.

In accordance with an eighth aspect of the present invention, the feature candidates generated by the feature generator unit includes a feature function discriminating a color of the tumor.

In accordance with an ninth aspect of the present invention, the feature determining unit compares the signal of each pixel included in the learning patterns calculated by the learning pattern input unit with a predetermined threshold value.

In accordance with a tenth aspect of the present invention, the feature determining unit compares the signal of each pixel included in the learning patterns calculated by the learning pattern input unit with a mean value of signals of pixels in the proximity of the pixel.

In accordance with an eleventh aspect of the present invention, the feature determining unit conducts operation for each of the learning patterns using a predetermined noise parameter for each of the feature candidates.

In accordance with a twelfth aspect of the present invention, the feature determining unit calculates, as the feature of each of the learning patterns corresponding to each of the feature candidates, a probability with which the feature of the learning pattern takes a predetermined value.

In accordance with a thirteenth aspect of the present invention, when the learning patterns can be classified irrespectively of the values of the features, the category table generator unit substitutes a redundant term for the value of the feature at an associated position of the category table.

In accordance with a fourteenth aspect of the present invention, each of the features of the input patterns is a value of a probability with which the feature at an order takes a predetermined value; and the diagnosis unit calculates, by use of the features, a probability with which each of the feature patterns contained in the category table takes a predetermined value of class information, the probability being used for decision.

In accordance with a fifteenth aspect of the present invention, there is provided a pathological diagnosis support program for use with a pathological diagnosis support device including a learning pattern input unit for obtaining from a pathological image to be used for learning, images centered on a tumor and inputting thereto the images as learning patterns; a learning pattern storage unit for storing and keeping the learning patterns to which class information is attached; a feature candidate generator unit for generating a plurality of feature candidates; a feature determining unit for determining a feature set of features suitable for diagnosis using the feature candidates generated by the feature candidate generator unit; a feature storage unit for storing and keeping the set of features determined by the feature determining unit; a category table generator unit for generating a category table; a pattern input unit for obtaining, from a pathological image to be diagnosed, images centered on a tumor candidate and inputting the images as input patterns; a feature extracting unit for extracting features from the input patterns; and a diagnosis unit for conducting diagnosis using the features. The program includes processing in which the feature determining unit calculates a feature of each of the learning patterns corresponding to each of the feature candidates and determines as a first feature of the feature set, a feature candidate for which a mutual information quantity with respect to the class information of a set of the learning patterns takes a maximum value; and sequentially determines, under a condition that the determined feature is known, as a subsequent feature of the feature set, a feature candidate for which mutual information quantity between a feature of each learning pattern corresponding to each feature candidate and the class information of an associated one of the learning patterns takes a maximum value; processing in which the category table generator unit calculates each feature of each of the learning patterns using the feature set and classifies the patterns using the category table including each feature of the learning patterns and the class information; processing in which the feature extracting unit calculates each feature of the input patterns using the feature set.

In accordance with a sixteenth aspect of the present invention, the program includes processing in which the diagnosis unit diagnoses the input patterns according a result of the diagnosis and the category table.

In accordance with a seventeenth aspect of the present invention, the program includes processing in which the feature determining means prepares a predetermined number of sets for a transition of the learning pattern according to a value of the feature, calculates the feature of each of the learning patterns, determines the feature candidate, distributes the learning pattern with a weight according to the feature thus determined, sequentially causes a transition of the learning pattern to one of the sets corresponding to the feature, and sequentially determines the feature candidate under a condition that information about the sets respectively containing the learning patterns and the determined feature are known, and processing in which the diagnosis means causes a transition of each of the input patterns according to each feature of the input patterns and a transition table sequentially having recorded a set to which the learning pattern belongs at determination of each feature of the feature set and diagnoses the input patterns according a set to which the input pattern belongs as a result of the transition In accordance with an eighteenth aspect of the present invention, the program includes processing in which the feature determining means prepares a predetermined number of sets for a transition of the learning pattern according to a value of the feature, calculates the feature of each of the learning patterns, determines the feature candidate, distributes the learning pattern with a weight according to the feature thus determined, sequentially causes a transition of the learning pattern to one of the sets corresponding to the feature, and sequentially determines the feature candidate under a condition that information about the sets respectively containing the learning patterns and the determined feature are known, processing in which the feature extracting means calculates the feature that indicates a probability with which the feature at an order takes a predetermined value, and processing in which the diagnosis means calculates, according to each feature of the input patterns and a transition table sequentially having recorded a set to which the learning pattern belongs at determination of each feature of the feature set, a probability with which the input pattern includes predetermined class information and then conducts the diagnosis.

In accordance with a nineteenth aspect of the present invention, the learning pattern input unit and the pattern input unit includes processing to select, from R, G, and B values of each pixel in the pathological image stained in advance, pixels belonging to a color region to which a cell nucleus of a predetermined tumor belongs; processing to calculate distance between a center of distribution of the color region and each pixel belonging to the color region; processing to assign a signal to the pixel according to the distance; processing to detect a peak of distribution of the signals in the pathological image; and processing to input an image centered on the peak as the learning pattern.

In accordance with a twentieth aspect of the present invention, the feature candidates generated by the feature generator unit includes a feature candidate obtained using a complex Gabor function as a feature extraction function.

In accordance with a twenty first aspect of the present invention, the feature candidates generated by the feature generator unit includes a feature candidate obtained using a feature extraction function obtained by normalizing a complex Gabor function.

In accordance with a twenty second aspect of the present invention, the feature candidates generated by the feature generator unit includes a feature function discriminating a color of the tumor.

In accordance with a twenty third aspect of the present invention, the pathological diagnosis support program further includes processing in which the feature determining unit compares the signal of each pixel included in the learning patterns calculated by the learning pattern input unit with a predetermined threshold value.

In accordance with a twenty fourth aspect of the present invention, the pathological diagnosis support program further includes processing in which the feature determining unit compares the signal of each pixel included in the learning patterns calculated by the learning pattern input unit with a mean value of signals of pixels in the proximity of the pixel.

In accordance with a twenty fifth aspect of the present invention, the pathological diagnosis support program further includes processing in which the feature determining unit conducts operation for each of the learning patterns using a predetermined noise parameter for each of the feature candidates.

In accordance with a twenty sixth aspect of the present invention, the pathological diagnosis support program further includes processing in which the feature determining unit calculates, as the feature of each of the learning patterns corresponding to each of the feature candidates, a probability with which the feature of the learning pattern takes a predetermined value.

In accordance with a twenty seventh aspect of the present invention, the pathological diagnosis support program further includes processing in which when the learning patterns can be classified irrespectively of the values of the features, the category table generator unit substitutes a redundant term for the value of the feature at an associated position of the category table.

In accordance with a twenty eighth aspect of the present invention, in the pathological diagnosis support program each of the features of the input patterns is a value of a probability with which the feature at an order takes a predetermined value, the program further comprising processing in which the diagnosis unit calculates, by use of the features, a probability with which each of the feature patterns contained in the category table takes a predetermined value of class information, the probability being used for decision.

In accordance with a twenty ninth aspect of the present invention, there is provided a pathological diagnosis support method for use with a pathological diagnosis support device including a learning pattern input unit for obtaining from a pathological image to be used for learning, images centered on a tumor and inputting thereto the images as learning patterns; a learning pattern storage unit for storing and keeping the learning patterns to which class information is attached; a feature candidate generator unit for generating a plurality of feature candidates; a feature determining unit for determining a feature set of features suitable for diagnosis using the feature candidates generated by the feature a candidate generator unit; a feature storage unit for storing and keeping the set of features determined by the feature determining unit; a category table generator unit for generating a category table; a pattern input unit for obtaining, from a pathological image to be diagnosed, images centered on a tumor candidate and inputting the images as input patterns; a feature extracting unit for extracting features from the input patterns; and a diagnosis unit for conducting diagnosis using the features. The method includes a step in which the feature determining unit calculates a feature of each of the learning patterns corresponding to each of the feature candidates and determines as a first feature of the feature set, a feature candidate for which a mutual information quantity with respect to the class information of a set of the learning patterns takes a maximum value; and sequentially determines, under a condition that the determined feature is known, as a subsequent feature of the feature set, a feature candidate for which mutual information quantity between a feature of each learning pattern corresponding to each feature candidate and the class information of an associated one of the learning patterns takes a maximum value; a step in which the category table generator unit calculates each feature of each of the learning patterns using the feature set and classifies the patterns using the category table including each feature of the learning patterns and the class information; a step in which the feature extracting unit calculates each feature of the input patterns using the feature set.

In accordance with a thirtieth aspect of the present invention, the method further includes a step in which the diagnosis unit diagnoses the input patterns according a result of the diagnosis and the category table.

In accordance with a thirty first aspect of the present invention, in the first step the feature determining means prepares a predetermined number of sets for a transition of the learning pattern according to a value of the feature, calculates the feature of each of the learning patterns, determines the feature candidate, distributes the learning pattern with a weight according to the feature thus determined, sequentially causes a transition of the learning pattern to one of the sets corresponding to the feature, and sequentially determines the feature candidate under a condition that information about the sets respectively containing the learning patterns and the determined feature are known, and the method further comprising a fourth step in which the diagnosis means causes a transition of each of the input patterns according to each feature of the input patterns and a transition table sequentially having recorded a set to which the learning pattern belongs at determination of each feature of the feature set and diagnoses the input patterns according a set to which the input pattern belongs as a result of the transition.

In accordance with a thirty second aspect of the present invention, in the first step the feature determining means prepares a predetermined number of sets for a transition of the learning pattern according to a value of the feature, calculates the feature of each of the learning patterns, determines the feature candidate, distributes the learning pattern with a weight according to the feature thus determined, sequentially causes a transition of the learning pattern to one of the sets corresponding to the feature, and sequentially determines the feature candidate under a condition that information about the sets respectively containing the learning patterns and the determined feature are known, and in the third step the feature extracting means calculates the feature that indicates a probability with which the feature at an order takes a predetermined value, and the method further comprises a fourth step in which the diagnosis means calculates, according to each feature of the input patterns and a transition table sequentially having recorded a set to which the learning pattern belongs at determination of each feature of the feature set, a probability with which the input pattern includes predetermined class information and then conducts the diagnosis.

In accordance with a thirty-third aspect of the present invention, the pathological diagnosis support method further includes steps to be executed by the learning pattern input unit and the pattern input unit. The steps includes a step of selecting, from R, G, and B values of each pixel in the pathological image stained in advance, pixels belonging to a color region to which a cell nucleus of a predetermined tumor belongs; a step of calculating distance between a center of distribution of the color region and each pixel belonging to the color region; a step of assigning a signal to the pixel according to the distance; a step of detecting a peak of distribution of the signals in the pathological image; and a step of inputting an image centered on the peak as the learning pattern.

In accordance with a thirty-fourth aspect of the present invention, the feature candidates generated by the feature generator unit includes a feature candidate obtained using a complex Gabor function as a feature extraction function.

In accordance with a thirty-fifth aspect of the present invention, the feature candidates generated by the feature generator unit includes a feature candidate obtained using a feature extraction function obtained by normalizing a complex Gabor function.

In accordance with a thirty-sixth aspect of the present invention, the feature candidates generated by the feature generator unit includes a feature function discriminating a color of the tumor.

In accordance with a thirty-seventh aspect of the present invention, the pathological diagnosis support method further includes a step in which the feature determining unit compares the signal of each pixel included in the learning patterns calculated by the learning pattern input unit with a predetermined threshold value.

In accordance with a thirty-eighth aspect of the present invention, the pathological diagnosis support method further includes a step in which the feature determining unit compares the signal of each pixel included in the learning patterns calculated by the learning pattern input unit with a mean value of signals of pixels in the proximity of the pixel.

In accordance with a thirty-ninth aspect of the present invention, the pathological diagnosis support method further includes a step in which the feature determining unit conducts operation for each of the learning patterns using a predetermined noise parameter for each of the feature candidates.

In accordance with a fortieth aspect of the present invention, the pathological diagnosis support method further includes a step in which the feature determining unit calculates, as the feature of each of the learning patterns corresponding to each of the feature candidates, a probability with which the feature of the learning pattern takes a predetermined value.

In accordance with a forty first aspect of the present invention, the pathological diagnosis support method further includes a step in which when the learning patterns can be classified irrespectively of the values of the features, the category table generator unit substitutes a redundant term for the value of the feature at an associated position of the category table.

In accordance with a forty-second aspect of the present invention, each of the features of the input patterns is a value of a probability with which the feature at an order takes a predetermined value. The method further includes a step in which the diagnosis unit calculates, by use of the features, a probability with which each of the feature patterns contained in the category table takes a predetermined value of class information, the probability being used for decision.

In accordance with a forty third aspect of the present invention, there is provided a pathological diagnosis support system including an information processing terminal for keeping pathological image data including a pathological image and information unique to a patient attached to the image; and a pathological diagnosis server for diagnosing the pathological image data. The server includes a pathological diagnosis support device according to one of claims 1 to 13 for diagnosing the pathological image contained in the pathological image data; and a diagnosis result storage unit for storing a diagnosis result from the pathological diagnosis support device together with the information unique to the patient. The information processing terminal requests the pathological diagnosis server to transmit to the terminal the diagnosis result together with the information unique to the patient, and the pathological diagnosis server compares the information unique to the patient received from the terminal with the information unique to the patient stored together with the diagnosis result and then transmits the diagnosis result to the terminal if the information unique to the patient received from the terminal matches the information unique to the patient stored together with the diagnosis result.

In accordance with a forty-fourth aspect of the present invention, the pathological diagnosis support system further includes an accounting server for keeping amounts of use charge respectively of the pathological diagnosis support device and the information processing terminal.

In accordance with a forty-fifth aspect of the present invention, when the diagnosis result storage unit stores the diagnosis result, the accounting server accumulates an amount of use charge of the pathological diagnosis support system.

In accordance with a forty-sixth aspect of the present invention, when the information processing terminal receives the diagnosis result, the accounting server accumulates an amount of use charge of the information processing terminal.

In accordance with the present invention, in consideration of importance of changes taking place in a cell nucleus, peripheral tissues thereof, and the like in the discrimination of properties of a tumor, subimages primarily including cell nuclei, pores, cytoplasm, and interstitium are extracted from a pathological image, and the subimages are stored as learning patterns and input patterns. On the basis of the subimages, presence or absence of a tumor and benignity or malignity thereof can be determined with high accuracy in a short period of time.

BRIEF DESCRIPTION OF THE DRAWINGS

The objects and features of the present invention will become more apparent from the consideration of the following detailed description taken in conjunction with the accompanying drawings in which:

FIG. 1 is a schematic block diagram showing a configuration of a system to implement a first embodiment of a feature selection method in accordance with the present invention;

FIG. 12 is a diagram showing an example of a transition table created in accordance with the present invention;

FIG. 13 is a diagram showing another example of a transition table created in accordance with the present invention;

FIG. 17 is a block diagram to explain processing in the fourth embodiment of a pathological diagnosis support system in accordance with the present invention.

DESCRIPTION OF THE EMBODIMENTS

Figure 2:
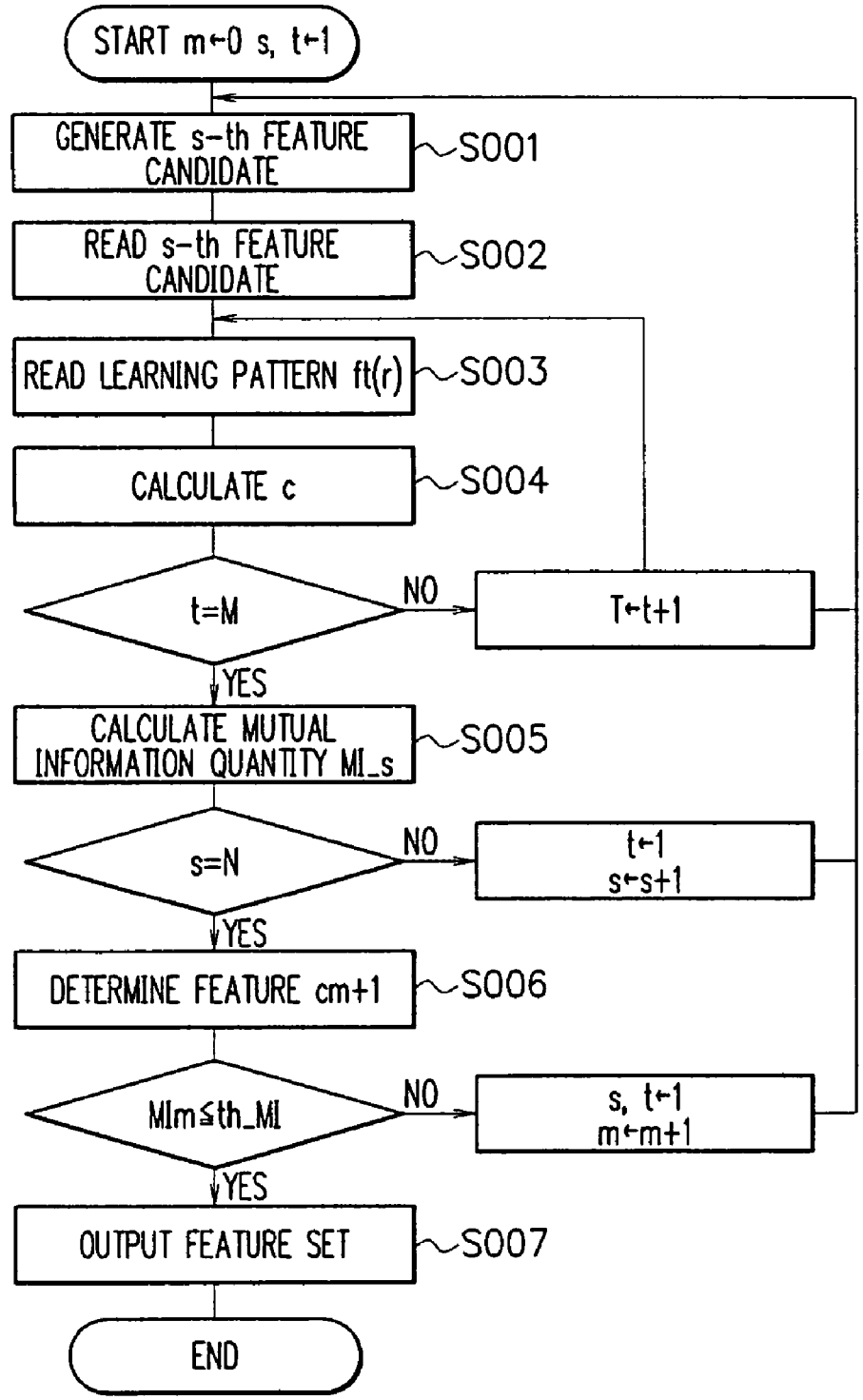
FIG. 2 is a flowchart to explain the first embodiment of a feature selection method in accordance with the present invention.

Referring next to the drawings, description will be given of an embodiment in accordance with the present invention.

FIG. 1 shows a configuration of an embodiment of a pathological diagnosis support device in accordance with the present invention. The device includes a learning pattern input unit 100, a learning pattern storage 101, a feature candidate generator 102, a feature determining unit 103, a feature storage 104, a category table generator 105, and a category table 106.

The input unit 100 extracts subimages mainly including cell nuclei, pores, cytoplasm, interstitium, and the like from a pathological image prepared for diagnosis and then stores the subimages in the learning pattern storage 101.

The storage 101 stores and keeps therein subimages for a desired number of learning steps or processes.

The feature candidate generator 102 is a device to sequentially create feature candidates using a predetermined number of feature parameter sets.

The feature determining device 103 determines an optimal feature set most suitable for the pattern discrimination using the feature candidates produced by the generator 102.

The feature storage 104 stores and keeps therein the feature set prepared by the feature determining unit 103.

The category table generator 105 creates a category table 106 for diagnosis using the feature set determined by the feature determining unit 103.

Referring next to FIG. 2, description will be given of a procedure of feature selection processing. FIG. 2 is a flowchart to explain the procedure of the feature selection processing executed in the embodiment of the pathological diagnosis support device.

The device sequentially creates feature candidates according to a large number (N) of feature parameter sets beforehand specified by the feature candidate generator 102 (S001). It is assumed in the N feature parameter sets of the embodiment that parameter sets 1 to N__1 are feature candidates regarding textures, parameter sets N__1 to N__1+N__2 are feature candidates for colors, and parameter sets N__1+N__2+1 to N are feature candidates regarding colors averaged using peripheral pixels. Although the feature candidates of three kinds are designated in this example, the feature candidates are not restricted by the example. That is, any element which is required to determine a feature of each pixel and contained in a pathological image can be generated as a feature candidate.

Next, description will be given of a method of determining features possessed by subimages according to feature candidates created by the feature candidate generator 102. The features are determined through either one of procedures 1 to 3 as below.

Procedure 1

The generator 102 first acquires an s-th feature parameter set (s=1 to N; processing starts with s=1). If s≦N__1, the unit 102 substitutes the s-th feature parameter set (k_s,r0_s,σ_s, th_s) for (k,r0, σ,th) to generate a complex Gabor function Gab and a Gaussian function G as shown in the following expression including parameters k, r0, and σ. For s≦N__1, subimages in colors stored as learning patterns in the learning pattern storage 101 are converted to gray-scale images according to a gray scale. A feature c is calculated using these images.

$$Gab(r; k, r_0, \sigma) = \exp(ik(r \cdot r_0) - |r - r_0|^2 / (2\sigma^2))  \quad (1)$$

$$G(r; r_0, \sigma) = \exp(-|r - r_0|^2 / (2\sigma^2) / (2\pi\sigma^2))$$

In expression (1), r=(x,y) indicates a position vector and $i^2=-1$. The feature candidate generator 102 delivers the complex Gabor function Gab and the Gaussian function G to the feature determining unit 103 together with a threshold parameter th and an identification number s of the feature candidate (step S002).

The learning pattern storage 101 sends to the unit 103 pairs of data items each including one of predetermined M subimages I_t(r,i_rgb) (t=1 to M) and a class qt (t=1 to M) to which the subimage belongs (step S003). In the description of the embodiment, the device uses two classes, i.e., q=0 or 1 for simplicity of description. The present invention is of course applicable to a case including three classes or more.

Using the subimages sequentially received from the learning image storage 101, the feature determining unit 103 calculates the feature c according to expression (2) and the complex Gabor function and the Gaussian function of expression (1) as well as other parameters (step S004). The calculation is repeatedly carried out for all learning patterns (M patterns) assuming that the t-th learning pattern is I_t(r,i_rgb).

$$a = \left| \sum_r I\_t(r, i\_rgb) Gab(r; k, r_0, \sigma) \right|^2 / \sum_r I\_t(r, i\_rgb)^2 G(r; r_0, \sigma) \quad (2)$$

$$c = 1 \text{ if } a \geq th,$$

$$c = 0 \text{ otherwise}$$

In expression (2), the denominator is a normalization or standardization factor to suppress variations in the value of "a" due to size of a learning pattern (luminance of an image). The normalization factor is omissible depending on learning patterns.

Procedure 2

The feature candidate generating unit 102 first acquires an s-th feature parameter set (s=1 to N; processing starts with s=1). If N__1+1≦s≦N__1+N__2, the unit 102 delivers the s-th feature parameter set (x_s,y_s,color_index) and an identification number s of the feature candidate to the feature determining unit 103 (step S002).

In this description, (x_s,y_s) indicates a position of a pixel determining feature c in a subimage, and color_index (=1 to 4) represents a color corresponding to the feature c.

Incidentally, color_index (=1 to 4) corresponds to colors as below.

A cell nucleus, cytoplasm, interstitium, and pores stained by hematoxylin and eosin (through HE staining) become blue, pink, light pink, and white, respectively. The colors are important factors to determine features of a pathological image. Color_index=1, 2, 3, 4 are assigned respectively to the colors of the cell nucleus, the cytoplasm, the interstitium, and the pores.

The learning pattern storage 101 delivers to the feature determining unit 103 data item pairs each of which includes one of the predetermined M learning patterns (color subimages) I_t(r,i_rgb) (r is pixel coordinates and i_rgb=1 to 3 are parameters designating r, g, b signals of pixels; t=1 to M) and a class qt (t=1 to M) to which the learning pattern belongs (step S003). In the embodiment, the device handles two classes, i.e., q=0 or 1 for simplicity of description. Naturally, the present invention can be applied to a case in which three classes or more are utilized.

For the learning patterns received from the learning image storage 101 (step S003), the feature determining unit 103 determines a color of a pixel placed at a position (x_s,y_s) in the learning pattern as below. If the color matches a color designated by a parameter color_index, the unit 103 sets the value of the feature c to one. Otherwise, the unit 103 sets the value to zero (step S004). Assuming a t-th learning pattern as I_t(r,i_rgb), the operation to determine the value of the feature c is repeatedly conducted for all learning patterns (M patterns).

For the color of a cell nucleus (color_index=1), a hematoxylin signal of each pixel calculated in the subimage detection is compared with a threshold value, e.g., 0.25. If the signal is more than the threshold value, the color of the pixel is assumed as that of the cell nucleus. To adaptively determine the threshold value, it is also possible that the values of the hematoxylin signals are accumulated or added to each other only for the pixels of which the hematoxylin signal value is at least, for example, 0.25 in the vicinity of the pixel under consideration to thereby calculate a mean value of the hematoxylin signal values. The mean value is multiplied by, for example, 0.9 to obtain a threshold value of the pixel. If the hematoxylin signal value of a pixel is more than the threshold value, the color of the pixel is regarded as the color of the nucleus.

For other than the cell nucleus, that is, for a pore, cytoplasm, and interstitium, the colors are classified according to predetermined color areas. For example, an HSV conversion is carried out for the R, G, and B values of each pixel to convert these values into values of hue (H=0 to 1), chroma (S=0 to 1), and lightness (V=0 to 1). If a pixel under consideration is not classified as a pixel having the color of the cell nucleus and has lightness V>0.92 and chroma S<0.1, the color of the pixel is regarded as that of the pore (color_index=2). If the pixel color is neither that of the cell nucleus nor that of the pore and has hue H<0.9 and lightness V<0.85, it is regarded that the pixel color is the color of the cytoplasm (color_index=3). In other than the above cases, the color of the pixel is assumed as that of the interstitium (color_index=4).

Procedure 3

The feature candidate generator 102 first obtains an s-th feature parameter set (s=1 to N; processing starts with s=1). If N_1+N_2+1≦s≦N, the unit 102 feeds the s-th feature parameter set (x_s,y_s,color_index,th_s) and an identification number s of the feature candidate to the feature determining unit 103 (step S002). In the description, (x_s,y_s) designates a position of a pixel determining the feature c in a subimage, color_index (=1 to 4) indicates a color corresponding to the feature c, and th represents a threshold parameter.

For the learning patterns received from the learning image storage 101 (step S0003), the feature determining unit 103 determines the feature c in a method described below (step S004). Assuming that a t-th learning pattern is represented as I_t(r,i_rgb), the operation to determine the feature c is repeatedly performed for all learning patterns (M patterns).

Processing to determine that the pixel color corresponds to color_index (=1 to 4) is almost same as that of procedure 2 and description thereof will be avoided.

First, the feature determining device 103 selects pixels in the proximity of a subimage pixel position (x_s,y_s), namely, pixels (x',y') within a range of, for example, two pixels apart from the pixel (x_s,y_s) in the x-axis direction and a y-axis direction, specifically, pixels satisfying a condition |x-x'|≦2 and |y-y'|≦2. For the pixels selected as above, the unit 103 makes a check to determine whether or not the pixels have a color matching the color designated by color_index. The unit 103 then counts the pixels existing in the neighbor of the pixel and having the color matching that of color_index to attain the number of pixels. The feature determining unit 103 then divides the number of pixels by the total number of pixels in the proximity of the pixel to thereby obtain a mean value. If the mean value exceeds the threshold parameter (th_s), the feature c is set to one. Otherwise, the feature c is set to zero.

The feature determining module 103 can determine the feature c of a pixel using a procedure described below in addition to the three procedures.

The module 103 conducts an HSV conversion for the R, G, and B values of each pixel in a subimage including a pixel under consideration to convert these values into values of hue (H=0 to 1), chroma (S=0 to 1), and lightness (V=0 to 1). The feature determining module 103 then represents the H, S, and V values in, for example, five levels. If, each of these values of the pixel is equal to or less than 0.2=⅕, the color of the pixel is represented as (1,1,1). If, the H and S values are equal to or less than 0.2 and the V value is 0.2<V≦0.4, the color of the pixel is expressed as (1,1,2). When a pixel at a position (x,y) in the subimage specified by (x,y,H',S',V') received from the feature candidate generator 102 has a color represented as (H',S',V'), the feature c is "1". Otherwise, the feature c is "0".

As above, when the feature c is calculated for each subimage using the s-th feature candidate (feature parameter set), the feature determining device 103 calculates according to expression (3) a mutual information quantity MI attained from the s-th feature candidate and then stores the quantity MI together with the identification number s of the feature candidate (step S005).

$$MI[Q; C] = H[Q] - <[Q \mid c]>_c \text{ where,} \quad (3)$$

$$H[Q] = -\sum_q P(q)\log P(q),$$

$$P(q) = M(q)/M$$

$$H[Q \mid c] = -\sum_q P(q \mid c)\log P(q \mid c),$$

$$P(q \mid c) = M(q \mid c)/M(c)$$

In this connection, Q is a set of classes {q=0,q=1} and M indicates a total number of subimages. M(q) is a total number of subimages belonging to a class q, M(c) indicates a total number of subimages of which the feature is c, and M(q,c) is a total number of subimages of which the feature is c and which belongs to the class q.

In expression (3), $<>_c$ indicates an averaging operation with respect to c and is calculated using expression (4).

$$<H[Q \mid c]>_c = -\sum_c P(c)H[Q \mid c], \quad (4)$$

$$P(c) = M(c)/M$$

Thereafter, a next feature candidate, i.e., an (s+1)-th feature candidate is received from the feature candidate generating device 102 and is repeatedly processed as above (steps S002 to S005). When the mutual information quantity MI is completely calculated for all of the feature candidates (N candidates), the feature determining device 103 compares the mutual information quantities MI of the respective feature candidates with each other to determine one of the feature candidate which has a maximum value of the mutual information quantity Max MI[Q;C]. The feature candidate is determined as a first feature of a feature set to be determined (step S006).

After the determination of the first feature, the device 103 determines a second feature. In a similar manner as described above, the feature determining unit 103 sequentially receives a feature candidate from the feature generator 102 (step S002) and calculates the feature c according to each subimage (steps S003 and S004). It is also possible depending on the available storage capacity that a calculation result of the feature c in step S004 at determination of the first feature is stored in the storage so that the feature determining unit 103 reads the data from the storage. When the feature c is calculated for each subimage, the device 103 calculates, using the s-th feature parameter set, a mutual information quantity $MI_2$ obtained from the s-th feature candidate according to expression (5) under a condition that the already determined first feature c1 is known, and then stores the quantity $MI_2$ together with an identification number s of the feature candidate (step S005).

$$MI_2[Q; C | C_1] = <H[Q | c_1]>_{c_1} - <H[Q | (c, c_1)]>_{c_1-c} \quad (5)$$

where, $$H[Q | c1] = -\sum_q P(q | c_1) \log P(q | c_1),$$

$$P(q | c_1) = M(q, c_1) / M(c_1)$$

$$H[Q | c, c1] = -\sum_q P(q | c, c_1) \log P(q | c, c_1),$$

$$P(q | c, c_1) = M(q, c, c_1) / M(c, c_1)$$

In expression (5), M(c1) is a total number of subimages of which the first feature is c1, $M(q,c_1)$ indicates a total number of subimages of which the first feature is c1 and which belongs to the class q. M(c,c1) indicates a total number of subimages of which the feature is c and of which the first feature is c1 and M(q,c,c1) is a total number of subimages of which the feature is c, of which the first feature is c1, and which belongs to the class q.

Through the above operation, a next feature candidate, namely, an (s+1)-th feature candidate is received from the feature candidate generating device 102 and is repeatedly processed in a similar fashion (steps S002 to S005). When the mutual information quantity MI is completely calculated for the feature candidates (N candidates), the feature determining device 103 compares the conditional mutual information quantities $MI_2$ of the respective feature candidates, which are obtained from the feature candidates, with each other to determine one of the feature candidate which has a maximum value of the mutual information quantity. The feature candidate is determined as a second feature of a feature set to be determined (step S006).

When an m-th feature is determined through a similar procedure, a feature candidate which maximizes the evaluation function $MI_{m+1}$ of expression (6) is adopted as an (m+1)-st feature c.

$$MI_{m+1}[Q; C | C_1, C_2, \ldots, C_m] = <H[Q | c_1, c_2, \ldots, c_m]>_{(c_1,c_2,\ldots,cm)} - \quad (6)$$
$$<H[Q | c, c_2, \ldots, c_m]>_{(c_1,c_2,\ldots,cm)}$$

In expression (6), $MI_{m+1}$ represents an information quantity obtained from the feature c under a condition that the features (c1,c2, . . . ,cm) are known. The processing is continuously executed until the obtained information quantity (additional information quantity) is less than a predetermined threshold value MI_th even if a new feature is selected. When the threshold value MI_th is set to, for example, zero, the processing procedure is repeatedly conducted to determine a next feature until the obtained information quantity (additional information quantity) becomes zero, that is, until the end condition is satisfied.

On the other hand, the feature determining procedure is terminated when the end condition is satisfied. The parameters of each feature set determined as above are stored in the feature storage 104 (step S007).

In variations of the feature selection method, there can be considered a procedure capable of reducing the number of feature candidates created by the feature candidate generator 102. For example, for each complex Gabor function, the intra-class mean value of the values of "a" calculated using expression (2) is beforehand prepared for a class of q=0 and a class of q=1 such that the threshold value MI_th is set to an intermediate value between the two intra-class mean values. Also, for example, when the mutual information quantity MI is calculated for each complex Gabor function using expression (3) at determination of the first feature, a threshold value MI_th which gives a maximum information quantity MI for each feature candidate is recorded. When the second and subsequent features are determined, the threshold value MI_th is kept fixed in the processing.

Although a complex Gabor function is employed as a feature extraction function to obtain feature candidates in the embodiment, another feature extraction function may be additionally employed. Depending on cases, only such feature extraction function is used to obtain feature candidates.

There may be favorably considered, for example, a variation in which a subspace is formed for each class such that an index indicating distance to the subspace is added to the feature candidate. Furthermore, it may also possible to add to the feature candidates, weighted mean luminance in a neighborhood of a point calculated using a Gaussian function or normalized weighted mean luminance where the weighted mean luminance in a neighborhood of a point calculated using a Gaussian function is normalized by mean luminance calculated using a Gaussian function of a wider range (i.e., an index representing whether the neighborhood of the point is brighter or darker than a periphery thereof). Moreover, standard features used in diagnosis can be added to the feature candidates.

Figures 4, 5:
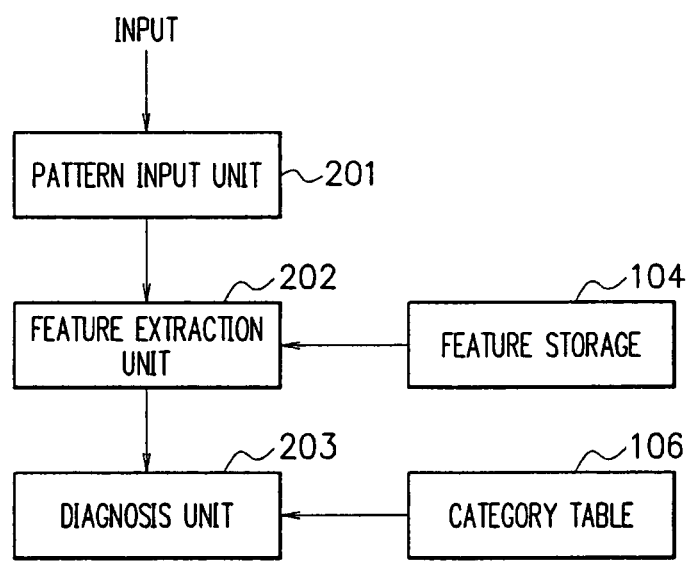
FIG. 4 is a diagram showing an example of a category table generated in accordance with the present invention.
FIG. 5 is a block diagram showing a configuration of a first embodiment of a system to conduct diagnosis in accordance with the present invention.

When the feature determination processing is completed and the feature sets thus determined are stored in the feature storage 104, it is possible to produce a category table 106 shown in FIG. 4 for pattern discrimination or identification. Description will now be given of processing for the category table generator 105 activated by a desired unit to create the category table 106.

The table generator 105 first receives each subimage from the learning pattern storage 101 and each parameter of the feature set from the feature storage 104 (it is assumed that the number of determined features are n in total) and stores the received items in the category table 106 together with the feature values (c1,c2, . . . ,cn) for each subimage.

The procedure makes it possible to produce a category table 106 uniquely classifying each subimage. However, more favorably, it is desirable to use a redundant term, i.e., a don't care term. For example, when a subimage can be classified using only the feature values (c1,c2, . . . ,cn) ranging from the first feature value to the i-th feature value, the values of the (i+1)-st and subsequent feature vectors are replaced by a symbol indicating "don't care" in the category table 106.

Figure 3:
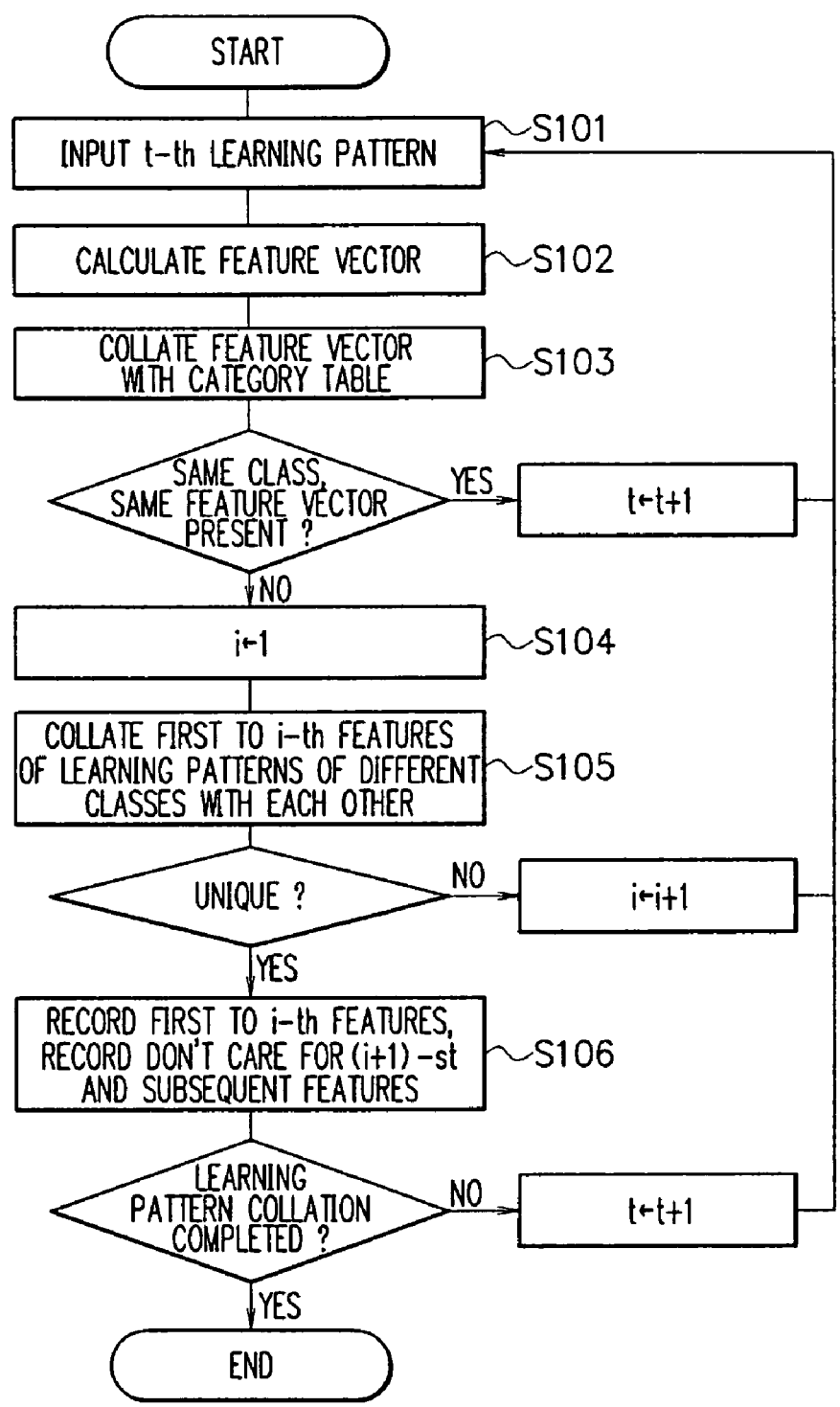
FIG. 3 is a flowchart showing an example of processing to create a category table in accordance with the present invention.

Referring next to FIG. 3, description will be given of a procedure to generate a category table 106 by use of the redundant term, i.e., don't care. FIG. 3 shows the procedure of creating the category table 106 in the embodiment.

The table generator 105 first calculates a feature vector (c1,c2, . . . ,cn) using the parameters of the feature set stored in the feature storage 104 (steps S101 and S102).

The generator 105 makes a check to determine whether or not the category table 106 includes a subimage having a feature vector matching the feature vector above (step S103).

When a field of the table 106 contains the symbol indicating "don't care", any value corresponding thereto is regarded as a matching value.

As a result of the determination, if the category table 106 includes a subimage having a feature vector matching the calculated feature vector, control returns to step S300 without recording the subimage in the table 106 to receive a next subimage.

On the other hand, if the matching subimage is absent, the category table generating unit 105 sets an increment variable i to "1" (i=1; step S104) to execute processing as follows. The generator 105 looks for subimages that belong to a class (for example, q=1) different from another class (for example, q=0) to which the subimage under consideration belongs and that include the first to i-th features ($c_1, c_2, \ldots, c_i$) all matching those of the subimage (step S105).

As a result, if such subimage is absent, the first to i-th feature values ($c_1, c_2, \ldots, c_i$) are recorded in the category table 106 together with a sign (e.g., q=0) of the class to which the subimage belongs. The symbol indicating "don't care" is recorded as the values of the (i+1)-st and the subsequent feature vectors (step S106). Control returns to step S300 to receive a next input subimage.

If such subimage is present, one is added to the increment variable i and control returns to step S304. That is, the increment of the value of i is successively executed until the inputted subimage becomes distinct from other subimages by the i-th feature value.

The processing is repeatedly executed for all subimages. In the procedure, there occurs a case in which it is not possible to classify all subimages. For example, in some cases, subimages belonging to mutually different classes possess an equal feature vector. In this case, the processing is executed, for example, as follows. The numbers of the subimages belonging to the respective classes are counted. The class to which a larger number of subimages belong is determined as a class associated with the feature vector.

There may also be adopted a method in which while incrementing the value of i, patterns for which the features $c_1$ to $c_i$ match each other are classified into a group (to sequentially obtain a group including a smaller number of subimages). When one group includes only one subimage, the (i+1)-st and subsequent features of the subimage are set as don't care terms.

FIG. 4 shows an example of the category table 106 employed in accordance with the present invention. Referring to FIG. 4, the table 106 stores entries each of which includes a class identification mark q of each subimage and a feature vector ($c_1, c_2, \ldots, c_n$). In this table, an asterisk indicates "don't care".

Referring next to the drawings, description will be given of a diagnosis method of a pathological image using the category table.

FIG. 5 shows in a block diagram a processing flow of the diagnosis method in accordance with the present invention. The flow includes a pattern input unit 201, a feature extraction unit 202, and a diagnosis unit 203. There are also included a feature storage 104 to store a determined feature set to be used by the unit 202 for feature extraction and a category table 106 prepared in advance for the unit 203 to conduct diagnosis.

The pattern input unit 201 is a constituent component to input a subimage from a desired medium. The unit 201 of the embodiment is arranged to input an image or a subimage of a cell of a pathological tissue centered on a cell nucleus. However, images are not restricted to nuclei. That is, images of cell nuclei, pores, cytoplasm, or interstitium may be adopted to facilitate pathological judgement or decision by a pathological expert in the diagnosis of pathological tissues.

The feature extraction unit 202 is a device which extracts, according to a subimage sent from the pattern input unit, a feature of the subimage using the determined feature set.

The diagnosis unit 203 is a module to diagnose information represented by the subimage, according to the feature from the feature extraction unit 202.

In the diagnosis processing, on the basis of the feature obtained by the pattern input unit 201, a subimage is acquired to be fed to the feature extraction module 202.

For the subimage, the unit 202 calculates a feature vector of the subimage using a feature set (determined in the feature determining method) determined through procedure 1, 2, or 3 stored in the feature storage 104 and then delivers a result of the calculation to the diagnosis module 203.

Referring to the category table 106, the module 203 retrieves therefrom an entry matching the feature vector and reads a class mark to output the mark as a diagnosis result. If the entry obtained from the table 106 contains "don't care", the diagnosis unit 503 determines that the entry matches the feature vector irrespective of the value of the feature.

To further clarify an advantage of the present invention to determine a feature of a subimage and to judge an image through the procedure, description will be given of difference between the present invention and a conventional method using a decision tree (ID3, C4.5).

Procedures of ID3 and the like are similar to those of the present invention in that the classification rule in each node of the decision tree is determined according to a criterion of information quantity maximization. However, in the methods of ID3 and C4.5, the classification rule, which is "feature" in terms of the description in the specification of the present invention, is determined for each node. For example, when a second feature is determined after determination of a first feature $c_1$, the classification rule (feature) varies in the determination between when $c_1$ is one and when $c_1$ is zero. In contrast therewith, if a substantially equal node depth is used, any arbitrary n-th features are determined to be equal to each other. This is a remarkable difference between the present invention and the conventional method.

In either one of the methods, the learning patterns are completely classified. However, there appears a considerable difference in performance of discrimination for subimages not learned yet. Assuming that the tree depths are substantially equal (n) to each other in both methods for simplicity of description, while $2^n$ features are determined in ID3 or C4.5, only n features are determined in accordance with the present invention. That is, the present invention is simpler in structure than the conventional method. The difference between the numbers of determined features exponentially increases as the problems become more complex and the decision tree required for the procedure becomes deeper.

It has been known as "Occam's rasor" that if two classifying devices have equal performance for learning patterns, the classifying device in a simpler configuration is superior in the performance of discrimination for subimages not learned yet. In this point, the feature selection method and the diagnosis method using the method in accordance with the present invention are superior to the prior art. Particularly, the performance of discrimination for subimages not learned yet is considerably increased as compared with the conventional method.

Description will now be given of processing to extract a subimage from a pathological image in the learning pattern input unit 100 and the pattern input unit 201. In the description of the embodiment, the system extracts a subimage centered on a cell nucleus. However, the present invention is not restricted by the embodiment. That is, the system may extract as a subimage a morphological feature part to which a pathological expert pays attention in the observation of a pathological image such as a pore, cytoplasm, and interstitium.

The processing to extract a subimage centered on a cell nucleus includes a step of calculating hematoxylin signals using the R, G, and B signals of each pixel in a pathological image and a step of detecting a central position of the cell nucleus according to a distribution of hematoxylin signals of respective pixels in the image. Actually, the system executes processing such as processing to smooth the hematoxylin signals. In the pathological image used to extract a cell nucleus, the cell nucleus is stained in blue using hematoxylin as a staining agent.

Figure 6:
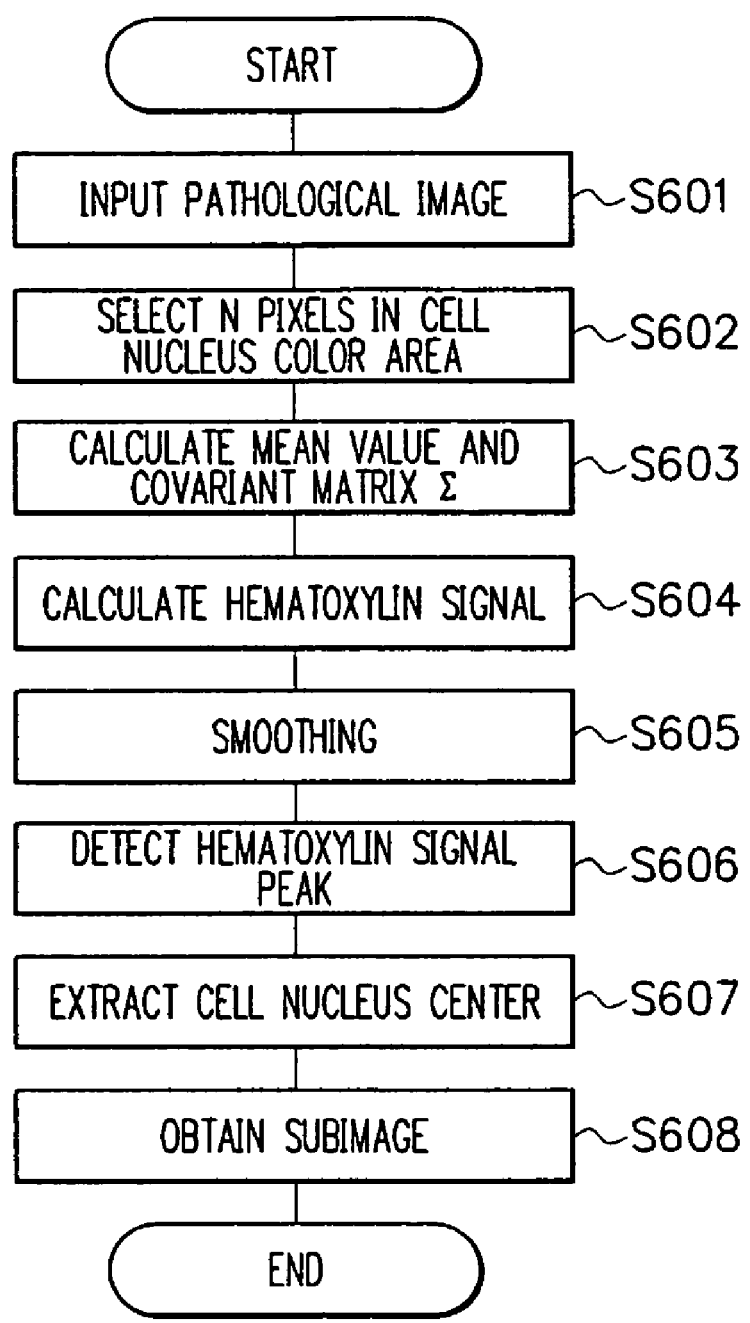
FIG. 6 is a flowchart showing an example of processing to extract subimages in accordance with the present invention.

Referring next to FIG. 6, description will be given of processing to extract a subimage in the learning pattern input module 100 and the pattern input module 201.

When a pathological image is received as an input (step S601), the modules 100 and 201 assign a hematoxylin signal to each pixel of the pathological image in which the cell nucleus is stained in blue.

According to the R, G, and B values of each pixel (R=0 to 255, G=0 to 255, B=0 to 255 when 24 bits are used), there is calculated a hematoxylin signal which takes a value of 1.0 in a region of the blue cell nucleus and a value of 0 in the other regions (a region stained in pink by eosin and a white region). In this processing, a check is made to determine a color distribution of the cell nucleus in an RGB space represented by R, G, and B values, and distance between the RGB value of each pixel and a center of the distribution is calculated. Specifically, the RGB value of each pixel is checked. If the value is associated with a position near the center of the color distribution of the cell nucleus in the RGB space, a hematoxylin signal having a large value near one is assigned to the pixel. If the value is at a position apart from the center of the color distribution, a hematoxylin signal having a small value near zero is assigned to the pixel. However, since the result of the staining of the cell nucleus varies between samples depending on the staining operation or the like, the color distribution of the cell nucleus is calculated in an adaptive method.

That is, by referring to the color region of the cell nucleus beforehand determined, only pixels each having the RGB value in the color region of the cell nucleus are selected as pixels representing the color of the cell nucleus.

The color region of the cell nucleus is beforehand determined as below. First, the system collects images of cell nuclei in which the stained state thereof vary due to the staining operation or the like. The RGB value is checked for each pixel in the cell nucleus region of each image. At the same time, a check is made to determine the RGB value for pixels in a region stained by eosin in the image and for pixels in a white region of the image. The processing then determines the color region of the cell nucleus which includes no or few regions stained by eosin and which includes pixels of the cell nucleus region.

Specifically, the learning pattern input module 100 and the pattern input module 201 assigns a hematoxylin signal to each pixel as below.

First, by referring to the color region of the cell nucleus beforehand determined, N pixels each having the RGB value in the color region of the cell nucleus are selected from the pathological image supplied to the modules 100 and 201 (step S602). Assume that the RGB value of each of the selected N pixels includes Ri, Gi, Bi (i=1 to N). Using Ri, Gi, and Bi of each pixel (i=1 to N) and according to expression (7), a mean value $(R_0,G_0,B_0)$ and a covariance matrix $\Sigma$ of Ri, Gi, and Bi are calculated (step S603).

$R_0 = 1/N \Sigma_i R_i, G_0 = 1/N \Sigma_i G_i, B_0 = 1/N \Sigma_i B_i,$ $$\Sigma = 1/N \Sigma_i (R_i - R_0, G_i - G_0, B_i - B_0)^T (R_i - R_0, G_i - G_0, B_i - B_0) \quad (7)$$

In expression (7), T is a symbol indicating transposition of a vector. Using the covariance matrix $\Sigma$ and according to expression (7), distance L between each pixel (R,G,B) and the mean value $(R_0,G_0,B_0)$ and the hematoxylin signal (Hema) are calculated (step S604).

$\frac{1}{2}(R-R_0,G-G_0,B-B_0)\Sigma^{-1}(R-R_0,G-G_0,B-B_0)^T$ $$\text{Hema} = \exp(-\frac{1}{2}(R-R_0,G-G_0,B-B_0)\Sigma^{-1}(R-R_0,G-G_0, B-B_0)^T) \quad (8)$$

Description will next be given of processing to detect a central position of the cell nucleus using the distribution of hematoxylin signals calculated for the respective signals according to expression (8).

Assume that the hematoxylin signal obtained for each pixel using expression (8) is represented as Hema($\vec{r}$). In the expression, $\vec{r}=(x,y)$ indicates a position vector of a position of a pixel in the pathological image. Using a smoothing mask $M_{low}$ and according to expression (9), a smoothing operation is conducted for Hema($\vec{r}$) (step S605) to obtain a peak value resultant from the smoothing, and the peak value is set as the central position of the cell nucleus (step S606).

$$\text{Hema}'(r) = \sum_{\vec{r}'} \text{Hema}(\vec{r}' - \vec{r}) M_{low}(\vec{r}') \quad (9)$$

In the expression, the smoothing mask $M_{low}$ may be implemented using, for example, a function of expression (10).

$M_{low}(\vec{r}') = M_0(\vec{r}',S_{ex}) - M_0(\vec{r}',S_{in}),$ $$M_0(\vec{r}',s) = 1/l (\text{when } |\vec{r}'|^2 \leq s^2), 0 (\text{otherwise}) \quad (10)$$

The normalization factor 1/l is determined as below.

$$\sum_{\vec{r}'} M_0(\vec{r}', s) = 1 \quad (11)$$

In the expression, $S_{ex}$ and $S_{in}$ are parameters determined in advance. Ordinarily, $S_{ex}$ is set to about a value of typical size (radius) of a cell nucleus and $S_{in}$ is set to 1.2 times that of $S_{ex}$.

After the hematoxylin signal (Hema') is attained for each pixel, if the value of Hema' of a point under consideration is more than a predetermined threshold value, e.g., 0.25 and more than the value of Hema' at any point in the neighborhood thereof, for example, within three pixels from the point along the x and y coordinates, the point is detected as a peak to be set as a central point of the cell nucleus (step S607).

In the processing, the hematoxylin signal smoothing and the peak detection may be accomplished as below in consideration of a large variation in size of the cell nucleus. Using a plurality of, e.g., three kinds of smoothing masks having mutually different sizes (parameters $S_{ex}$ and $S_{in}$), the smoothing operation and the peak detection are carried out to detect a peak position. The peak position obtained as a result is set as the center of the cell nucleus.

The learning pattern input unit 100 and the pattern input unit 201 detect the center of a cell nucleus by executing the processing for the pathological image supplied thereto. The units 100 and 201 then obtain a large number of images of a predetermined size, equal to the number of cell nucleus's centers resultant from the processing, from the pathological image, where the cell nuclei are at the center of the images, to extract each of the subimages as a learning pattern or an input pattern (step S608).

Second Embodiment

Next, description will be given of a second embodiment in which effective noise is added to learning patterns in accordance with the present invention.

The system configuration of the second embodiment is almost the same as that of the first embodiment (reference is to be made to FIG. 1). The processing flow of the second embodiment is substantially equal to that of the first embodiment (reference is to be made to FIGS. 2 to 6). Description will be given of only the difference between the first and second embodiments.

According to procedure 1 of the embodiment, there has been prepared a noise parameter ($s \leq N\_1$) in the feature parameter set in addition to ($k\_s$, $r0\_s$, $\sigma\_s$, $th\_s$) for the feature candidate generator 102. As in step S001 of the first embodiment, the generator 102 substitutes an s-th feature parameter set ($k\_s$, $r0\_s$, $\sigma\_s$, $th\_s$, $\sigma n\_s$) for ($k$, $r0$, $\sigma$, $th$), where the initial value of s is one, to thereby generate the complex Gabor function and the Gaussian function according to expression (1). The generating unit 102 then delivers the Gabor function, the Gaussian function, the threshold value parameter th, the noise parameter $\sigma n$, and the identification number s of the feature candidate to the feature determining unit 103 (step S002 of FIG. 2).

The unit 103 sequentially receives learning patterns from the learning pattern storage 101 (step S003 of FIG. 2) to calculate a feature b of each learning pattern using the Gabor function and the Gaussian function as below (step S004 of FIG. 2). In the following expression, a t-th learning pattern is expressed as $I\_t(r, i\_rgb)$, where t ranges from one to M.

$$a = \left| \sum_r I\_t(r, i\_rgb) Gab(r; k, r_0, \sigma) \right|^2 \Big/ \sum_r I\_t(r, i\_rgb)^2 G(r; r_0, \sigma) \quad (12)$$
$$b = Erf((a - th)/\sigma_n)$$

In expression (12), Erf(x) is an error function. This function may be replaced by another nonlinear function taking a value ranging from 0 to one, for example, a sigmoid function.

After the feature b is obtained for each learning pattern using the s-th feature parameter set, a check is made to determine whether or not the value of the feature b is b ($0 \leq b \leq 1$). If this is the case, it is assumed that the feature c of the learning pattern takes a value of one with a probability of b and a value of zero with a probability of (1-b).

The method of calculating the feature c in second procedure of the second embodiment is almost the same as that of the first embodiment and hence description thereof will be avoided.

In procedure 3 of the embodiment, there has been set a noise parameter $\sigma\_s$ in the feature parameter set ($N\_1 + N\_2 \leq s \leq N$) in addition to ($x\_s$, $y\_s$, color_index, $th\_s$) for the feature candidate generator 102 ($N\_1 + N\_2 \leq s \leq N$). The generating unit 102 feeds the feature parameter set ($x\_s$, $y\_s$, color_index, $th\_s$), the noise parameter $\sigma n\_s$, and the identification number s of the feature candidate to the feature determining unit 103. Incidentally, ($x\_s$, $y\_s$) indicates a position of a pixel to determine the feature c in the subimage, color_index ranging from one to four is a color corresponding to the feature c, and $th\_s$ designates a threshold parameter.

The feature determining module 103 receives the feature parameter set ($x\_s$, $y\_s$, color_index, $th\_s$) and determines the feature of the pixel at the position of ($x\_s$, $y\_s$) as below.

The processing to determine that the pertinent pixel has a color corresponding to color_index is almost the same as that of procedure 2 of the first embodiment and hence description thereof will be avoided.

The feature determining module 103 first makes a check to determine whether or not any pixel in the vicinity of the position of ($x\_s$, $y\_s$) in the subimage, for example, a pixel ($x'\_s$, $y'\_s$) within a range of two pixels in the x and y coordinates from the position ($x\_s$, $y\_s$) of the pertinent pixel, that is, any pixel defined by $|x-x'| \leq 2$ and $|y-y'| \leq 2$ has a color specified by color_index. The feature determining unit 103 counts the number of pixels satisfying the above condition to obtain the number thereof. The unit 103 divides the number by the number of all pixels in the proximity of the pertinent pixel to calculate a mean value a. The feature determining unit 103 then assigns the mean value a, the threshold parameter $th\_s$, and the noise parameter $\sigma n\_s$ to expression (6) to obtain the feature b for each learning pattern.

After the feature b is calculated for each learning pattern by use of the s-th feature parameter set, it is assumed as in procedure 1 that if the value of the feature b is b ranging from zero to one, the feature c is one with a probability of b and is zero with a probability of (1-b).

When the feature b is attained in this fashion, the feature determining module 103 calculates the mutual information quantity MI using the s-th feature candidate according to expression (3) as below (step S005 of FIG. 2).

To calculate MI, M(c) of expression (3) is replaced in expression (3) by an expected value of the number of all learning patterns for which the feature is c and M(q,c) is replaced by an expected value of the number of all learning patterns for which the feature is c and which belong to the class q.

When the mutual information quantities are completely calculated for all feature candidates, the feature determining unit 103 conducts operation in substantially the same way as in the first embodiment. That is, the unit 103 compares the quantities thus obtained for the respective candidates with each other to determine the maximum information quantity. As a result, a feature candidate for which the maximum information quantity is attained is determined as a first feature in the feature set (step S006 of FIG. 2).

Subsequently, the processing is repeatedly executed in a similar fashion. When the features are acquired up to the m-th feature, an (m+1)-th feature $c_{m+1}$ is obtained, under a condition that the features up to the m-th feature ($c_1, c_2, \ldots, c_m$) are known, such that the maximum value of the information quantity $MI_{m+1}$ is obtained for the feature c. However, as in the determination of the first feature, the mutual information quantity is calculated by replacing the number of all learning patterns by the expected value of the total number of all learning patterns according to associated feature items. For example, to calculate MI2, M(c,c1) is replaced in expression (4) by "an expected value of the number of all learning patterns of which the feature is c and the first feature is c1". Moreover, M(q,c,c1) is replaced by "an expected value of the number of all learning patterns of which the feature is c and the first feature is c1 and which belong to class q".

As in the first embodiment, the processing procedure is continuously carried out until the information quantity, i.e., the additional information quantity attained for a new feature selected as above is less than a predetermined threshold value. When the completion condition is satisfied, the parameters of the determined feature set are recorded in the feature storage 104 (step S007 of FIG. 2).

Figure 7:
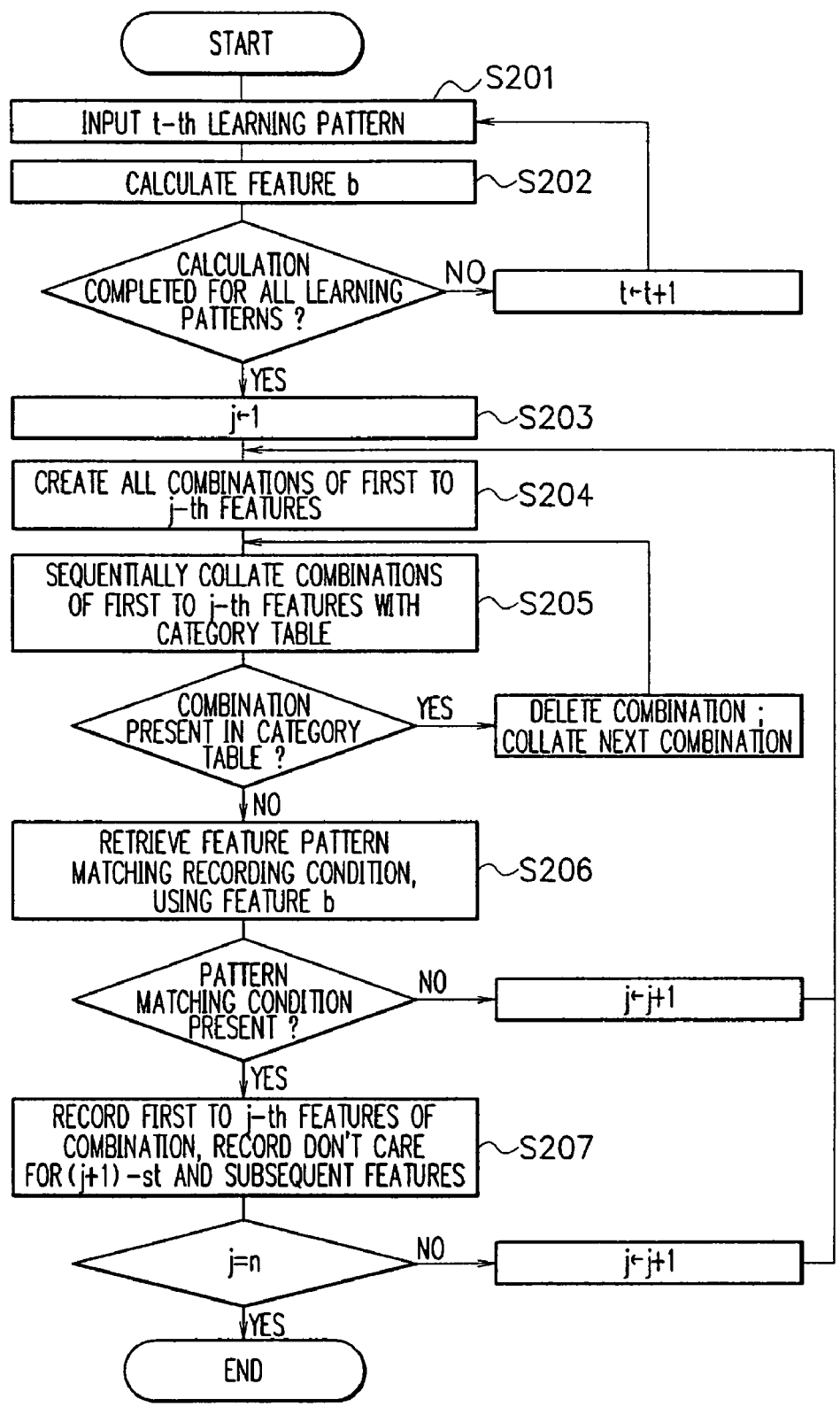
FIG. 7 is a flowchart showing another example of processing to create a category table in accordance with the present invention.

Referring now to the drawings, description will be given of a procedure to create another category table when the feature c is calculated in procedure 1, 2, or 3. FIG. 7 is a flowchart showing an example of processing to generate a category table in the embodiment. It is assumed that the feature determining module has determined n features and the category table has been initialized, i.e., the contents thereof have been cleared.

Referring to FIG. 7, the category table creating unit 105 calculates each feature bs (b1,b2, . . . ,bn) for each learning pattern according to expression (12) by use of the parameters of the feature set (steps S201 and S202). When the features bs are calculated for all learning patterns, the unit 105 determines probability bs with which the s-th feature cs is one and probability 1-bs with which the s-th feature cs is zero and then initializes the value of j to one. The unit 105 thereafter starts processing to select patterns to be recorded in the category table 106 (step S203).

The category table creation module 105 produces all combinations of the first to j-th features (c1,c2, . . . ,cj) in step S204. By sequentially collating the combinations of the first to j-th features with the feature vectors beforehand registered to the table 106 (step S205), the module 105 deletes or erases any combination therefrom that matches one of the feature vectors recorded in the table 106 (step S205-1). In the operation, if a symbol of "don't care" is in the table 106, it is assumed that a matching condition holds regardless of the value in the table 106.

For the remaining feature patterns (c1,c2, . . . ,cj), the unit 105 calculates an expected value using the features bs obtained for the learning patterns in step S202 to retrieve any feature pattern satisfying a condition under which the feature pattern is recorded in the category table 106 (step S206). More specifically, the category table creating unit 105 sequentially selects an appropriate feature pattern (c1, c2, . . . ,cj) from the remaining feature patterns to determine, according to the following conditions, a feature pattern as a pattern representing the class q to store the pattern together with the mark q in the category table 106 (step S207). The conditions for the feature pattern include (1) the feature pattern of which the expected value of the number of all learning patterns belonging to a class q is equal to or more than a predetermined threshold value and (2) the feature pattern of which the expected value of the number of all learning patterns belonging to each of the classes other than the class q is equal to or less than a predetermined threshold value. In the procedure, a symbol indicating "don't care" is written in the columns or fields of the (j+1)th to n-th features.

As a result of the retrieval, if it is not possible to obtain a feature pattern matching the condition, j is updated as j+1 and control returns to step S204 to create again all combinations of the first to j-th features (c1,c2, . . . ,cj). On the other hand, when the retrieval is finished for all combinations of the features up to the n-th features (j=n), the processing is terminated.

Referring again to FIG. 5, description will now be given of another diagnosis procedure in the embodiment when feature c is calculated according to procedure 1, 2 or 3.

For the input pattern delivered from the pattern input module 201, the feature extracting unit 202 calculates a feature vector (b1,b2, . . . ,bn) according to expression (6) by use of the feature set of procedure 1 or 3 stored in the feature storage 104 to feed the vector to the diagnosis module 203. It is assumed in this situation that the s-th feature cs (s=1 to n) is one with a probability of bs and is zero with a probability of (1-bs).

By referring to the category table 106, the diagnosis module 203 calculates a probability with which the input pattern belongs to each associated class, specifically, in a procedure described below.

Description will now be given of an operation to calculate the probability with which the input pattern belongs, for example, to the class q=0. The module 203 first reads all feature patterns (c1,c2, . . . cn) having the mark of q=0 from the category table 106. Assume that the first feature pattern is obtained as (c1,c2, . . . ,cn)=(1,0,*,*, . . . ,*), where an asterisk represents "don't care". Since the features c1 and c2 are respectively one and zero with a probability of b1 (1-b2) for the input pattern, the feature vector of the input pattern matches the feature pattern also with a probability of b1 (1-b2). In this connection, since the third and subsequent features are indicated as "don't care", the feature values thereof as a whole do not affect the probability.

According to the probabilities bs and (1-bs) calculated using the input pattern, the diagnosis module 203 obtains a probability with which the feature vector of the input pattern matches each feature pattern corresponding to q=0 to thereby attain the total of the probabilities. The total indicates a probability with which the input pattern belongs to the class q=0. The module 203 makes a comparison between the probabilities with which the input pattern belongs to the respective classes to produce as a comparison result a class associated with a maximum probability.

Depending on cases, it is naturally possible to beforehand determine a threshold value so that a rejection signal (indicating an event in which the determination is not possible) is outputted on the basis of a result of a comparison with the threshold value.

To reduce the processing time, there may be employed a method in which only the category table is created using the method of the second embodiment and the diagnosis processing is executed adopting the method of the first embodiment. In this case, the feature vectors for the input pattern are calculated according to expression (2).

According to the second embodiment of the present invention, there is obtained an advantage in which noise is effectively added to the learning patterns. This makes it possible to select a set of features having a larger margin. Therefore, as compared with the first embodiment, the second embodiment has an aspect that the performance of discrimination for patterns other than the learning patterns is improved.

Third Embodiment

Description will now be given of a third embodiment in accordance with the present invention by referring to the drawings. Also in this embodiment, the operation can be extended to handle three classes or more as in the first and second embodiments. However, in the description of the third embodiment, operation is conducted with two classes (q=0 or 1) for convenience of description.

Figure 8:
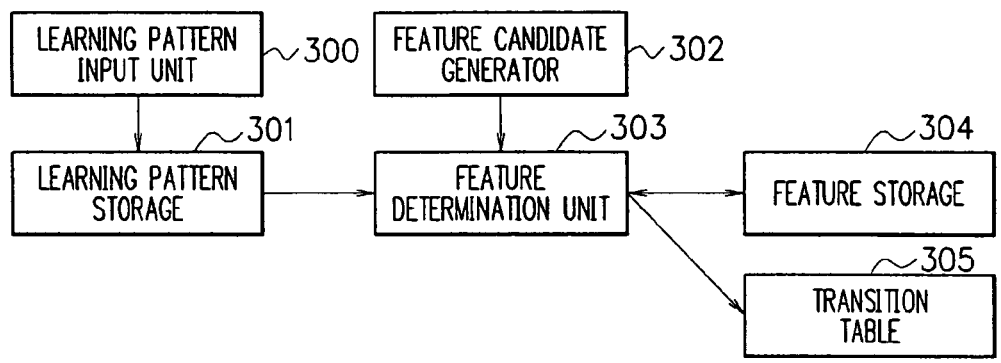
FIG. 8 is a block diagram showing a configuration of a system to implement a third embodiment of a feature selection method in accordance with the present invention.

FIG. 8 shows in a block diagram a system configuration of the third embodiment of the feature selection method in accordance with the present invention. The system of FIG. 8 includes a learning pattern input unit 300, a learning pattern storage 301, a feature candidate generator 302, a feature determining unit 303, a feature storage 304, and a transition table 305. Description of the same constituent components as those of the first and second embodiments will be avoided.

The feature determining unit 303 is a module to determine, using the feature candidates created by the feature candidate generator 302, an optimal feature set of features optimal for pattern discrimination. The module 303 produces a transition table 305 in which parameters obtained in a process of a feature determining procedure of the third embodiment are recorded.

The table 305 records parameters to be used in diagnosis processing, which will be described later.

Before the procedure, the parameters will be described.

Assume that there are prepared M learning parameters as well as set group Di (i=1 to L) and set group D'i (i=1 to L) associated with Di. L is a predetermined natural number and is 64 in the description of the third embodiment.

Referring next to the drawings, description will be given of a procedure of a feature selection method of the third embodiment. The procedure of the third embodiment up to the determination of the first feature is substantially equal to that of the second embodiment. Assume that when the feature c is calculated in procedure 2, the value of b is replaced by that of the feature c in the processing described below.

Figure 9:
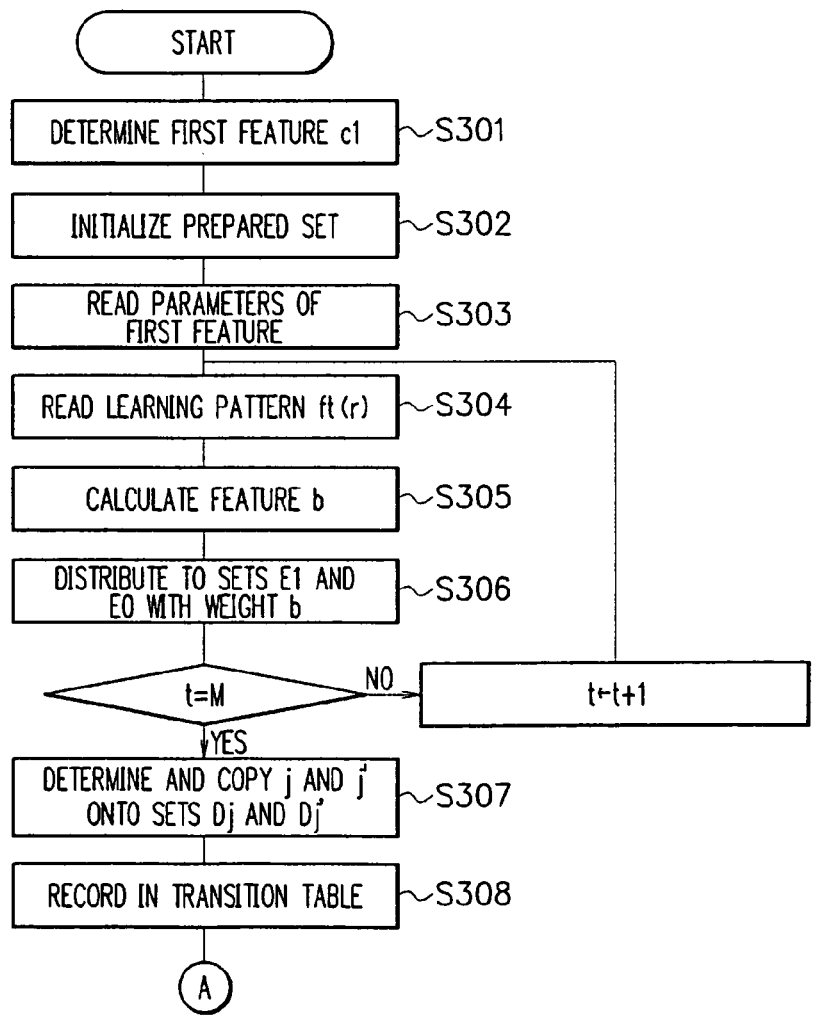
FIG. 9 is a flowchart to explain the third embodiment of a feature selection method in accordance with the present invention.
Figure 10:
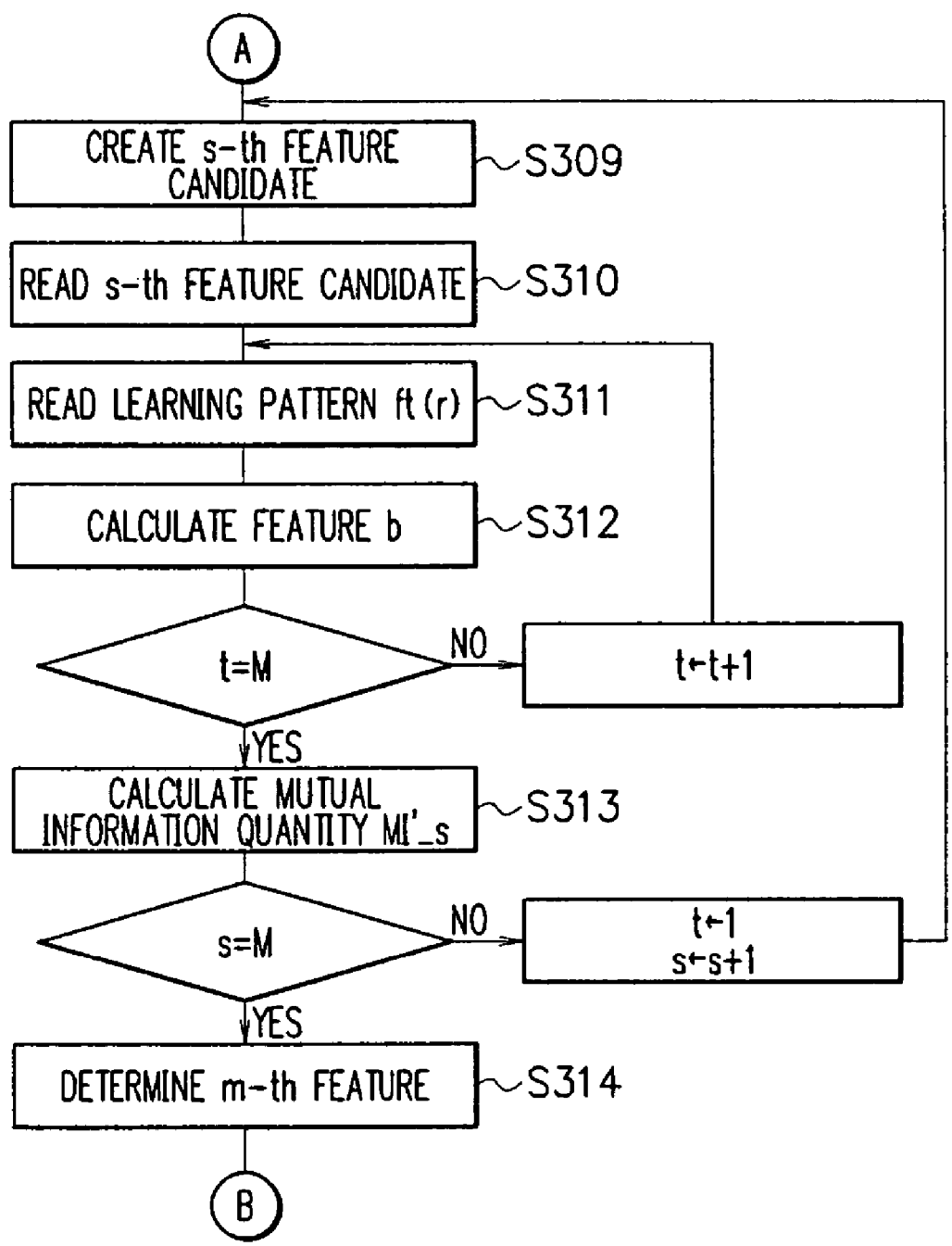
FIG. 10 is a flowchart to explain the third embodiment of a feature selection method in accordance with the present invention.
Figure 11:
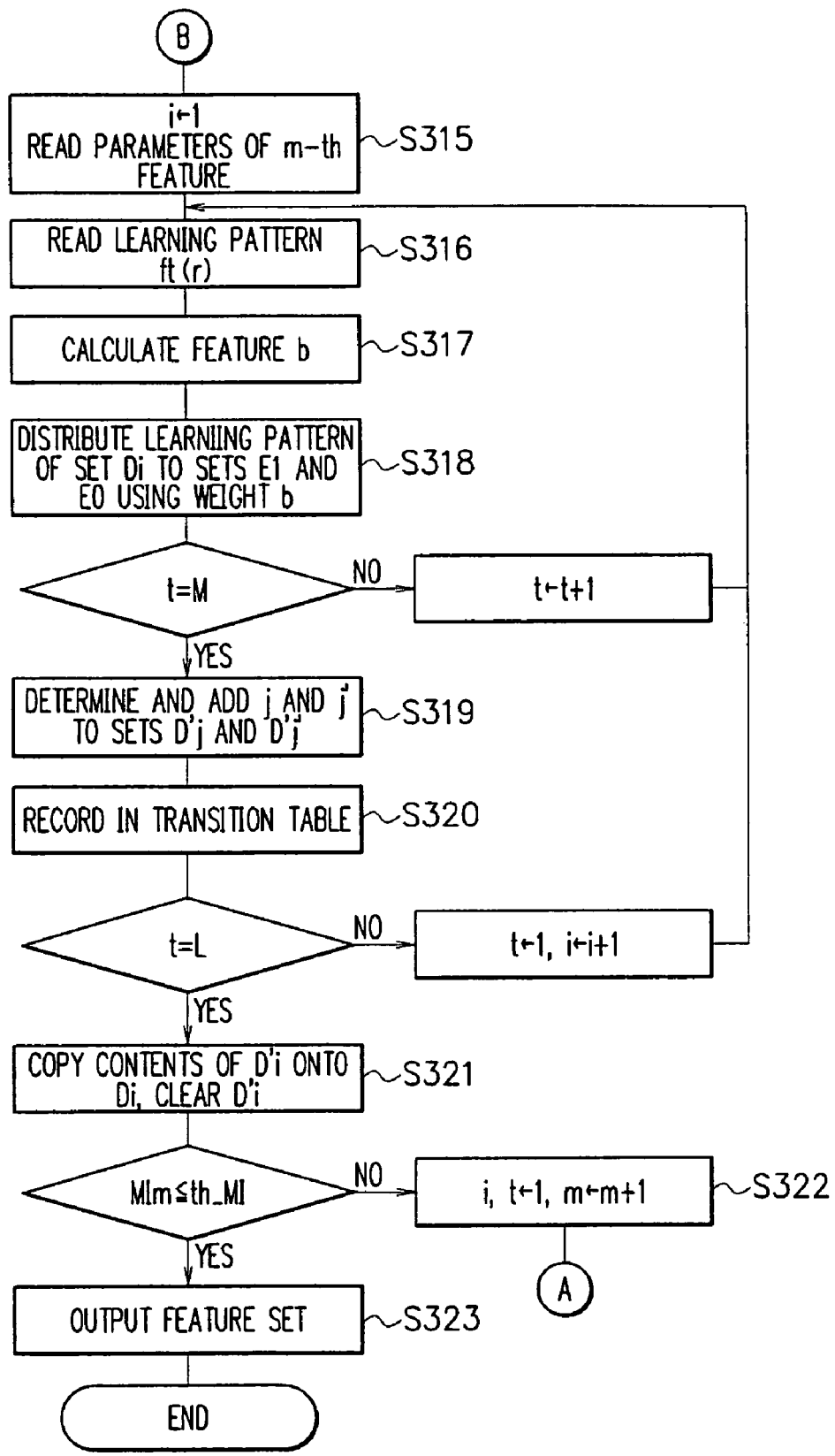
FIG. 11 is a flowchart to explain the third embodiment of a feature selection method in accordance with the present invention.

FIGS. 9 to 11 are flowcharts to explain a flow of processing of the feature selection method in accordance with the present invention. In FIG. 9, when the first feature is determined (step S301), the feature determining unit 303 initializes the sets Di and D'i (i=1 to L) in step S302. Since L=64 in this situation, the initialization is conducted for sets D1 to D64 and sets D'1 to D'64. That is, the contents of the sets are cleared to obtain empty sets.

Assume that a feature order parameter m is "two" so that the procedure starts using the second feature.

Using the first feature parameter beforehand determined and according to expression (12), the feature determining module 303 calculates the feature b for each learning pattern (steps S303 to S305).

The module 303 then distributes each learning pattern to the set E1 using a weight b and to the set E0 using a weight (1-b) in step S306.

When the processing is completely finished for all learning patterns, the module 303 calculates $P(q=1|E1)$ and $P(q=1|E0)$.

$$P(q=1|E_1) = M(q=1, E_1)/M(E_1)$$

$$P(q=1|E_0) = M(q=1, E_0)/M(E_0) \quad (13)$$

In the expression (13), M(E0) and M(E1) are totals of weights of the learning patterns belonging to the sets E0 and E1, respectively. M(q=1|E0) and M(q=1|E1) are totals of weights of the learning patterns which belong to the class of q=0 and which respectively belong to the sets E0 and E1.

The feature determining unit 303 then copies the contents of the sets E0 and E1 to which the learning patterns are distributed according to the weights as above respectively onto sets Dj and Dj' determined by the group of sets Di prepared in advance (step S307).

$$d\_(j-1) \leq P(q=1|E_0) < d\_j$$

$$d\_(j'-1) \leq P(q=1|E_1) < d\_j' \quad (14)$$

In expression (14), d_j indicates a constant (j=1 to L-1) determined as below. According to expression (15), the constant d_j takes a value ranging from 0 to one and increases substantially in a shape of S according to the value of j. For example, if P(q=1|E0)=0.15, there is determined j=30 which satisfies the first expression of expression (14) according to d_29=0.111..., d_30=0.2. Therefore, E0 is copied onto D30. Similarly, if P(q=1|E1)=0.7, there is determined j'=34 which satisfies the second expression of expression (14) according to d_33=0.666..., d_34=0.8. Therefore, E1 is copied onto D34.

$$0 = d\_0 < d\_1 < d\_2 < \ldots < d\_L = 1$$

$$d\_j = 2^{j-32}/(1+2^{j-32}) \quad (15)$$

The expression (15) is naturally determined according to the numbers of set Di and set D'i and for easy handling thereof in the third embodiment. However, the expression is not limitative at all.

The feature determining module 303 records (1,j,j') in the transition table 305 (step S307). For example, if j=30 and j'=34, (1,30,34) is written in the table 305 (reference is to be made to FIG. 12). The table 305 is used in the subsequent diagnosis processing and indicates transition as follows. If the first feature is c1=1, there occurs a transition to the set Dj. If the first feature is c1=0, there occurs a transition to the set Dj'.

Referring to FIG. 10, the module 303 first calculates, like in the second embodiment, the features b and c for each learning pattern using the s-th feature candidate (s is 1 to N; beginning at s=1) in steps S309 to S312. As in the operation of the second embodiment, it is assumed that when the feature b is calculated in procedure 1 or 3, the feature c is one with a probability of b and is zero with a probability of (1-b) for each learning pattern.

The feature determining unit 303 calculates the information quantity MI' obtained using the s-th feature candidate as below (step S313).

$$MI' = H_1 - \langle H_2 \rangle_c \text{ where,} \quad (16)$$

$$H_1 = -\sum_{q,i} P(q|D_i) \log P(q|D_j),$$

$$P(q|D_j) = M(q|D_j)/M(D_j)$$

$$H_2 = -\sum_{q,i} P(q|c, D_i) \log P(q|c, D_j),$$

$$P(q|c, D_j) = M(q, c, D_j)/M(c, D_j)$$

In expression (16), M(Di) indicates the total of weights of learning patterns contained in the set Di, and M(q,Di) is the total of weights for learning patterns which are contained in the set Di and which belong to the class q. However, the sum is calculated with respect to i only when M(Di) is not zero. M(c,Di) is an expected value of the total of weights of learning patterns for which the feature is c and which are contained in the set Di. M(q,c,Di) is an expected value of the total of weights of learning patterns for which the feature is c and which are contained in the set Di, the learning pattern belonging to class q.

In this manner, the feature b is attained for each learning pattern until s=N occurs. When the information quantities MI' are completely calculated for all feature candidates, the feature determining module 303 compares the information quantities with each other to select therefrom a feature candidate for which the maximum information quantity is obtained. The module 303 resultantly determines the feature candidate as an m-th feature of a feature set as a target of the processing (step S314).

When the m-th feature for which the maximum information quantity is acquired is thus determined, the module 303 conducts operation for all sets Di (D1 to D64) as follows.

Referring to FIG. 11, the feature determining unit 303 calculates the feature b for each learning pattern by use of the m-th feature parameter according to expression (12) and then distributes each learning pattern belonging to Di to the set E1 with a ratio of b and to the set E0 with a ratio of (1-b) in steps S315 to S318 (reference is to be made to FIG. 13).

The unit 303 then calculates P(q=1|E1) and P(q=1|E0) according to expression (13).

Thereafter, the feature determining unit 303 adds the contents of the sets E0 and E1 respectively to D'j and D'j' determined using the beforehand prepared sets D'j according to expression (14) in step S319. For example, as can be seen from FIG. 14, for P(q=1|E0)=0.05, the feature determining module 303 determines j=28 satisfying the first expression of expression (14), and adds E0 to D'28. Similarly, for P(q=1|E1)=0.3, the module 303 determines j'=31 satisfying the second expression of expression (14) to thereby add E1 to D'31 (reference is to be made to FIG. 14).

The module 303 records (m,i,j,j') in the transition table 305 (step S320). For example, if m=2, i=30, j=28, and j'=31, (j=28,j'=31) is stored at an associated position (m=2,i=30) as shown in the table 305. The recorded information indicates that a transition to the set Dj occurs if cm=1 for the m-th feature and a transition to the set Dj' takes place if cm=0 for the m-th feature. The information is utilized in the diagnosis processing, which will be described later.

Figure 14:
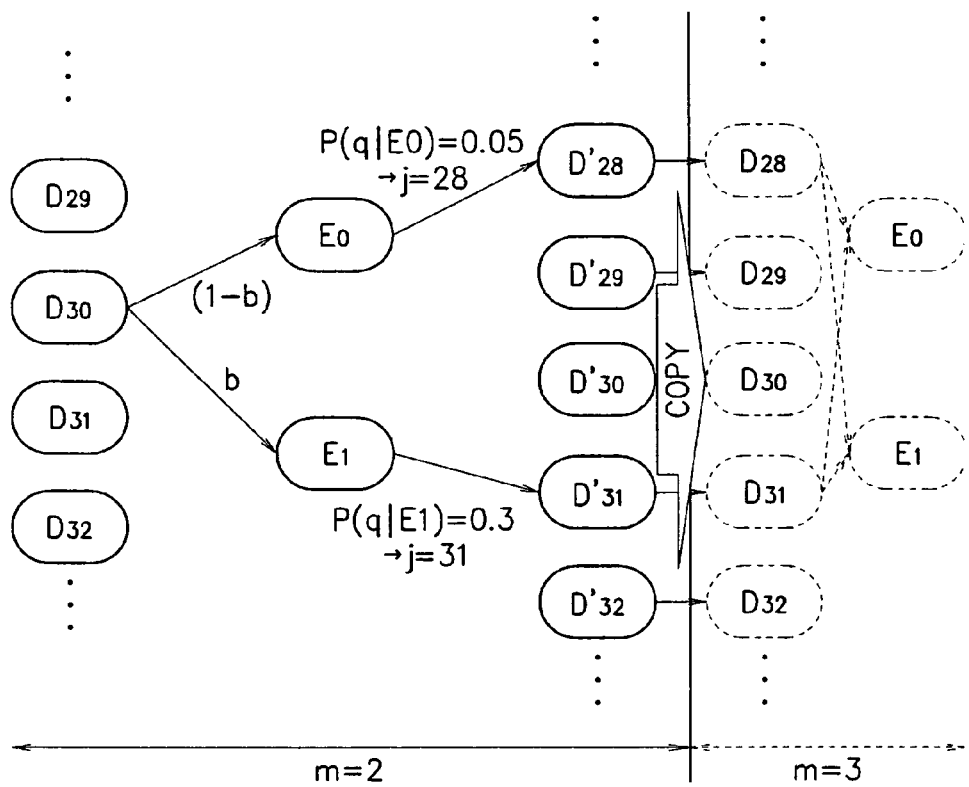
FIG. 14 is diagram briefly showing transitions between sets in the third embodiment in accordance with the present invention.

When the operation is completely finished for all sets Di (i=1 to L), the feature determining unit 303 copies the sets D'i (i=1 to L) onto the sets Di (i=1 to L) and then initializes or clears the sets D'i (i=1 to L) to determine a subsequent feature, i.e. an (m+1)-th feature in step S321 (reference is to be made to FIG. 14).

The processing is continuously executed until the information quantity (additional information quantity) obtained in step S314 is less than a predetermined threshold value MI_th even if a new feature is selected. Therefore, unless the completion condition is satisfied, the unit 303 sets m=m+1 and returns control to step S309 to determine a subsequent (m+1)-th feature (step S322)

On the other hand, when the completion condition is satisfied, the parameters of the determined feature set are written in the feature storage 304 (step S323).

Figure 12:
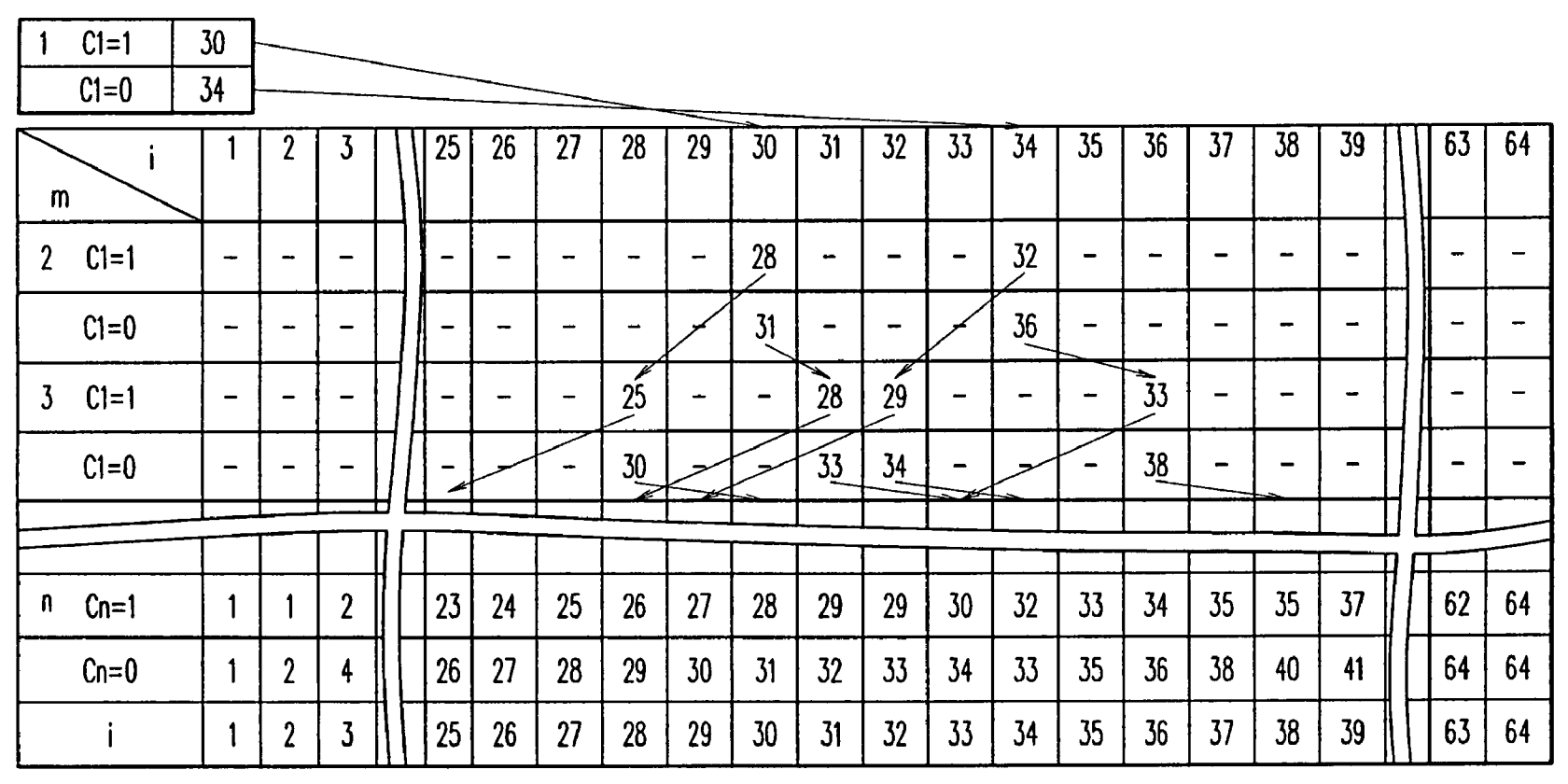

Description will next be given of the transition table generated for the determining operation in the third embodiment of the present invention. FIG. 12 shows an example of the transition table. As can be seen from FIG. 12, the table includes a first section indicating a set of transition destinations for the first feature and a second section designating a set of transition destinations for each of the second and subsequent features using a feature order parameter m, a set number parameter i, and a value Cm of each feature.

Referring to the first section of the transition table in FIG. 12, a column or field for c1=1 contains "30" and a column for c1=0 contains "34". This means that a transition to the set D30 occurs if the first feature is designated as c1=1 and a transition to the set D34 takes place if the first feature is specified as c1=0. In a column of m=2 and i=30 of the second section of the table, a column for c1=1 contains "28" and a column for c1=0 contains "31". This indicates that the pattern belonging to the set D30 takes a transition to the set D28 if the second feature is designated as c2=1 and to the set D31 if the second feature is specified as c2=0.

In the columns of the second section of the table in FIG. 12, a dash "-" indicates that the associated column is empty. For example, in the row (m=2) storing a transition destination according to the value of the second feature c2, the columns or fields other than the columns (i=30, 34) corresponding to the sets D30 and D34 contain a dash, namely, are empty fields. This is associated with a situation that the sets of transition destinations corresponding to the first feature are designated as "30" or "34". That is, according to the transition table of FIG. 12, the input pattern takes a transition in any situation to the set D30 or D34 according to the first feature, and hence it is not required to refer to the other fields.

The section of the sets of transition destinations for the first feature and the section of the sets of transition destinations for the second and subsequent features are separately stored in the transition table of FIG. 12. This however does not restrict the present invention. It is only required that the sets of transition destinations are indicated using the feature order parameter m, the set number parameter i, and the value Cm of each feature. For example, the first and second sections of the FIG. 12 may be unified into a table as shown in FIG. 13.

Figure 15:
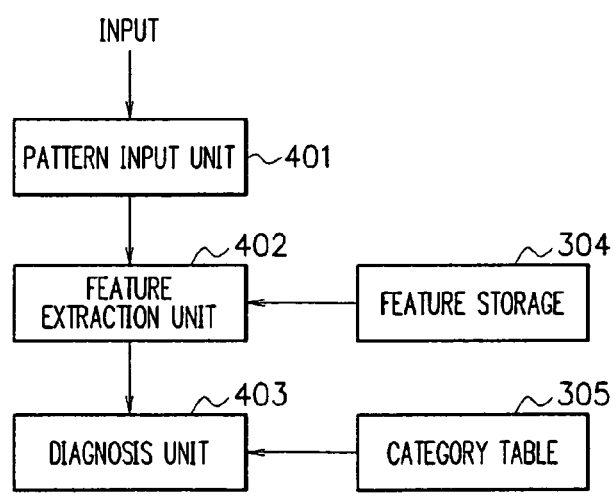
FIG. 15 is a block diagram showing a configuration of a third embodiment of a system to conduct diagnosis in accordance with the present invention.
Figure 16:
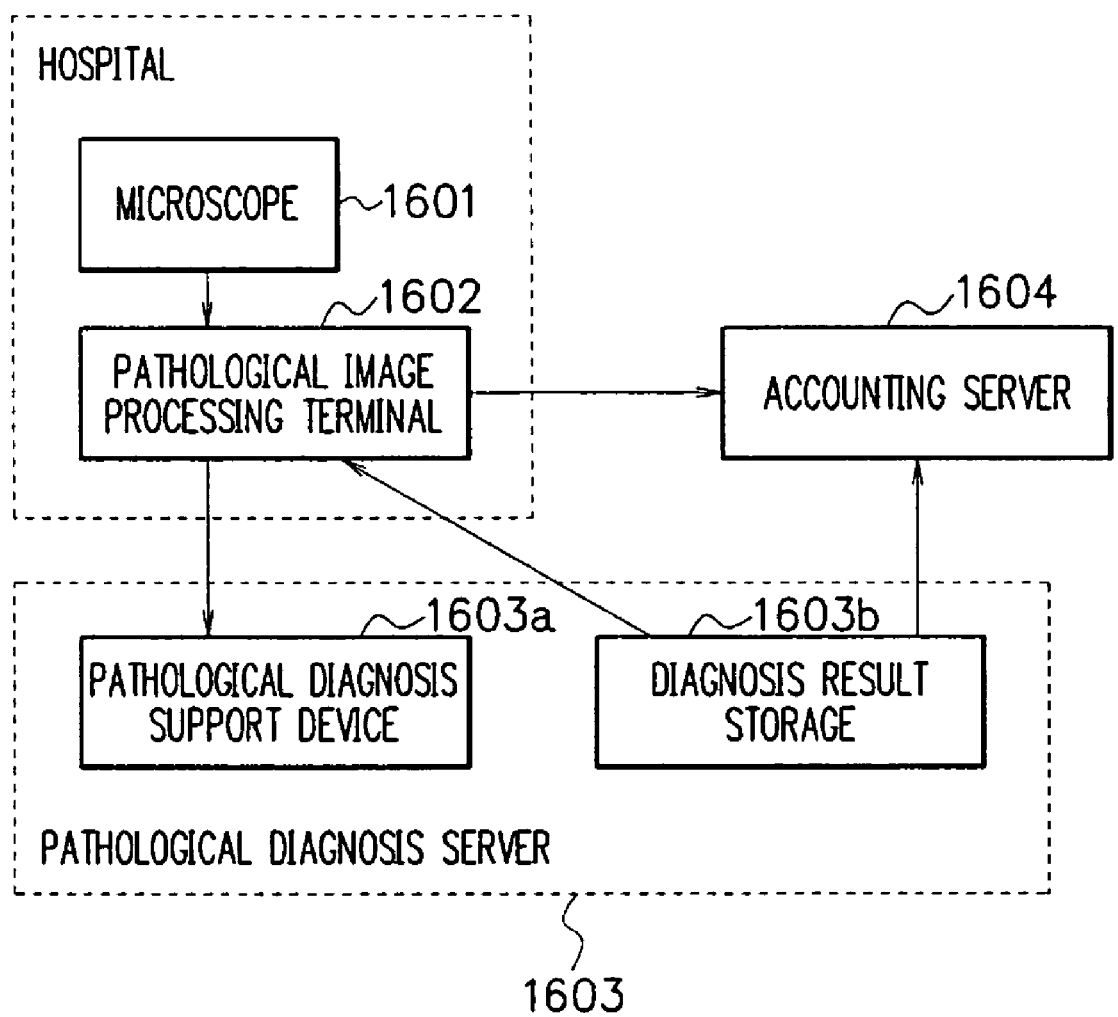
FIG. 16 is a block diagram showing a configuration of a fourth embodiment of a pathological diagnosis support system in accordance with the present invention.

Subsequently, description will be given of a diagnosis procedure in the third embodiment. FIG. 15 shows in a block diagram a diagnosis method of conducting diagnosis using the feature sets determined as above. The configuration of FIG. 15 includes a pattern input unit 401, a feature extracting unit 402, and a diagnosis unit 403 as well as a feature storage 304 from which the unit 402 extracts features, and a transition table 305 for the diagnosis unit 403 to conduct diagnosis.

In operation, the pattern input unit 401 receives an input pattern from a desired medium to send the pattern to the feature extracting module 402.

The module 402 receives the input pattern and calculates a feature vector (b1,b2, . . . ,bn) for the pattern according to expression (12) by use of the feature sets (determined in the feature determining method) which are obtained in procedure 1, 2, or 3 and which are stored in the feature storage 304. The feature vector is then delivered to the diagnosis module 403. It is assumed that when an i-th feature ci is calculated using procedure 2, the value bi is replaced by ci in the feature vector.

It is assumed in this situation that the feature cs (s≦N_1 or N_1+N_2≦s≦N) is one with a probability of bs and is zero with a probability of (1-bs). The diagnosis module 403 sequentially refers to the transition table 305 to calculate a probability with which the input pattern belongs to each associated class. This procedure is accomplished as follows.

The module 403 first reads a transition rule (1,j,j') corresponding to the first feature and causes the state to take a transition to a state j with a probability of b1 and to a state j' with a probability of (1-b1). The diagnosis module 403 then reads, assuming that the second feature c2 is one with a probability of b2 and is zero with a probability of (1-b2), a transition rule according to the second feature to cause another state transition. For example, when the transition rule for the second feature includes (2,j,k,k') and (2,j',k'',k'''), the state j is changed to the state k with a probability of b2 and to the state k' with a probability of (1-b2). The state j' is altered to the state k'' with a probability of b2 and to the state k''' with a probability of (1-b2). Therefore, in this case, the pattern is in the state k with a probability of b1·b2, in the state k' with a probability of b1 (1-b2), in the state k'' with a probability of (1-b1) b2, and in the state k''' with a probability of (1-b1)·(1-b2). The diagnosis module 403 similarly changes the state using the features up to the n-th feature by referring to the transition table.

Assume that as a result of the state transition carried out up to the n-th feature, the probability of presence of the pattern in each state j is calculated as P(j) (j=1 to L). The probability P(q=1) with which the input pattern belongs to the class q can be attained as below.

$$P(q=1) = \sum_{j=1,L} P(j)P(q=1\mid j) \text{ where,} \qquad (17)$$

$$P(q=1\mid j) = (d\_j + d\_(j-1))/2$$

If the probability P(q=1) is more than a predetermined threshold value, the diagnosis unit 403 determines that the input pattern belongs to class q=1 and produces a result of the determination. If the probability P(q=1) is less than the threshold value, the unit 403 determines "rejection" or "determination disabled" and produces a result of the determination. Naturally, various modifications are possible also in this case. For example, there may be disposed two threshold values including an adoption critical value and a rejection critical value. It is also possible that when the probability is in a boundary zone, the unit 403 assumes "determination disabled".

Although the probability P(q=1|j) is determined according to expression (17) in the third embodiment, the probability may also be attained by use of learning patterns. That is, the state of each learning pattern I_i(r,i_rgb) is changed using the transition table, and the probability (i,j) with which each pattern is finally in the state j is calculated according to the feature vector (b1,b2,...,bn) of the learning pattern. Next, the total of the values of P(i,j) is obtained only for the learning patterns belonging to class q=1 and is expressed as P1(j), and the total of the values of P(i,j) is obtained for all learning patterns and is indicated as Ptotal(j). The value of P(q=1|j) is attained as P(q=1|j)=P1(j)/Ptotal(j).

As a variation to reduce the processing time of diagnosis in the third embodiment, there may be employed a method in which only the transition table 305 is created by using the method of the this embodiment and the feature vector is calculated for the input pattern according to expression (2). Specifically, the determining operation does not include any probabilistic operation, and the diagnosis is conducted by changing the state in a deterministic fashion according to the feature vector obtained using expression (2). When the state is changed on the basis of the transition table, the state can be changed in a deterministic way at each operation stage. Therefore, when the state is changed using the features up to the n-th feature, the state is finally determined as a particular state j of the states 1 to L. A check is made to determine the value of P(q=1|j) of expression (17) corresponding to the state j. If the value is more than a predetermined threshold value, it is determined that the input pattern belongs to class q=1 and a result of the determination is produced.

In accordance with the third embodiment of the present invention, an advantage is attained in which noise is effectively added to the learning patterns as in the second embodiment. This leads to an advantage to select a set of features having a larger number of margins.

Additionally, the third embodiment has an advantage that the calculation steps for the feature selection can be remarkably reduced when compared with the second embodiment for the following reason. That is, even if the number n of the features to be selected increases, the calculation necessary for the feature selection can be implemented by the calculation (expression (16)) of the information quantity attained when at most L sets are subdivided according to features.

In the third embodiment, the information quantity is calculated while learning patterns, which were once classified, are merged appropriately with the sets Di. Therefore, it is avoidable that the number of learning patterns belonging to each set Di is extremely small. This resultantly suppresses an event in which a feature is selected depending on a learning pattern, leading to an advantage that the versatility is increased.

Fourth Embodiment

Description will now be given of a configuration and operation of a pathological diagnosis support system including a pathological diagnosis support device associated with the first to third embodiments.

Description will be given of a configuration of the pathological diagnosis support system according to the fourth embodiment.

The system includes a microscope 1601, a pathological image processing terminal 160, a pathological diagnosis support server 1603, and an accounting server 1604. The terminal 160 and the servers 1603 and 1604 are connected via a network to each other. The pathological diagnosis support server 1603 includes a pathological diagnosis support device 1603a and a diagnosis result storage 1603b associated with the first to third embodiments.

The microscope 1601 and the pathological image processing terminal 160 are installed in a medical institution such as a hospital. The microscope 1601 is a device to shoot a focus of a patient to produce a pathological image of the focus. The image is stored and is kept in the terminal 1602. The pathological image processing terminal 1602 adds information unique to the patient to the pathological image to create pathological image data and keeps the data therein. The terminal 1602 sends the data to the pathological diagnosis server 1603 and receives a result of diagnosis therefrom.

The server 1603 is installed in places such as a research institute and a diagnosis service firm. The pathological diagnosis support device 1603a receives the phathological image data from the terminal 1602 to extract subimages therefrom and then conducts diagnosis using the subimages to determine presence or absence of a tumor and malignity or benignity of the tumor if such tumor is present. Specific operation is almost the same as that described in conjunction with the first to third embodiments, and hence description thereof will be avoided.

The diagnosis storage 1603b stores the diagnosis result from the support device 1603a together with information unique to the associated patient. If necessary, a result of diagnosis made by a pathological expert can be added to the diagnosis result from the device 1603 to store the resultant data in the support device 1603b. When the terminal 1602 issues a request to the storage 1603b for the diagnosis result, the storage 1603b transmits a request to the terminal 1602 to send information unique to the patient to the storage 1603b. When the information is received from the terminal 1602, the storage 1603b compares the information with the information unique to the patient added to the diagnosis result. Only if the information matches those added to the diagnosis result, the storage 1603b transmits the diagnosis result to the terminal 1602.

The accounting server 1604 accumulates charges for using a system each time the diagnosis result is kept in the storage 1603b of the server 1603 to keep the result of the accumulation together with an amount of system rental charge and an amount of data update charge kept in the support device 1603a. Each time the terminal receives the diagnosis result, the accounting server 1604 keeps an amount of utilization charge of the microscope and the terminal 1602 installed in the hospital.

Referring next to FIG. 17, description will be given of specific operation of the pathological diagnosis support system associated with the fourth embodiment.

The microscope 1601 produces a pathological image of a focus of a patient (step S1701). Information unique to the patient is added to the image and then the resultant data is transferred to the pathological image processing terminal device 1602 to be stored therein as pathological image data (step S1702). The terminal 1602 sends the data to the pathological diagnosis server 1603 (step S1703). The server 1603 receives the data and extracts by the pathological diagnosis support device 1603a subimages from the pathological image contained in the data and then diagnoses the image (step S1704). A result of the diagnosis from the support device 1603a is stored in the diagnosis result storage 1603b together with the information unique to the patient contained in the pathological image data (step S1705). When the accounting server 1604 is connected to the server 1603, the accounting server 1604 accumulates the amount of system use charge to produce the total thereof each time the diagnosis result is stored in the storage 1603b (step S1706).

When the terminal 1602 requests the diagnosis server 1603 to send the diagnosis result (step S1707), the server 1603 issues a request to the terminal 1602 to input information unique to the patient. The server 1603 receives the information from the terminal and then compares the information with information unique to the patient attached to each diagnosis result (step S1708).

If the information from the terminal 102 matches information attached to the diagnosis result (yes in step S1708), the pathological diagnosis server 1603 transmits the diagnosis result stored in the storage 1603b to the terminal 1602 (step S1709). When the accounting server 1604 is connected to the terminal 1602, the accounting server 1604 accumulates the amount of use charge of the terminal 1602 to produce the total thereof each time the terminal 1602 receives the diagnosis result (step S1710). If the information from the terminal 102 is other than information attached to each diagnosis result (no in step S1708), the processing is terminated without transmitting the diagnosis result.

According to the fourth embodiment, even when a patient in a remote place regularly goes to a hospital as an outpatient, it is possible for the patient, if the pathological image processing terminal 1602 is installed in the hospital, to access via a network to the pathological diagnosis server 1603 to receive a diagnosis result in a short period of time. Moreover, since it is not required for the pathological expert to diagnose all pathological images obtained from the patient, the diagnosis load imposed on the expert can be mitigated. As the information unique to the patient is required when the diagnosis results are sent to the terminal 1602, it is possible to prevent leakage of the diagnosis result from the pathological diagnosis server 1603.

While the present invention has been described with reference to the particular illustrative embodiments, it is not to be restricted by those embodiments but only by the appended claims. It is to be appreciated that those skilled in the art can change or modify the embodiments without departing from the scope and spirit of the present invention.

What is claimed is:

1. A pathological diagnosis support device, comprising:
   learning pattern input means for obtaining images centered on a tumor from a pathological image and inputting thereto the images as learning patterns;
   learning pattern storage means for storing and keeping the learning patterns to which class information is attached;
   feature candidate generator means for generating a plurality of feature candidates;
   feature determining means for determining a feature set of features suitable for diagnosis using the feature candidates generated by the feature candidate generator means;
   feature storage means for storing and keeping the set of features determined by the feature determining means;
   category table generator means for generating a category table;
   pattern input means for obtaining, from a pathological image to be diagnosed, images centered on a tumor candidate and inputting the images as input patterns;
   feature extracting means for extracting features from the input patterns; and
   diagnosis means for conducting diagnosis using the features, wherein:
   the feature determining means calculates a feature of each of the learning patterns corresponding to each of the feature candidates and determines as a first feature of the feature set, a feature candidate for which a mutual information quantity with respect to the class information of a set of the learning patterns takes a maximum value; and sequentially determines, under a condition that the determined feature is known, as a subsequent feature of the feature set, a feature candidate for which mutual information quantity between a feature of each learning pattern corresponding to each feature candidate and the class information of an associated one of the learning patterns takes a maximum value;
   the category table generator means calculates each feature of each of the learning patterns using the feature set and classifies the patterns using the category table including each feature of the learning patterns and the class information; and
   the feature extracting means calculates each feature of the input patterns using the feature set,
   wherein the learning pattern input means and the pattern input means select, from R, G, and B values of each pixel in the pathological image stained in advance, pixels belonging to a color region to which a cell nucleus of a predetermined tumor belongs, calculate distance between a center of distribution of the color region and each pixel belonging to the color region, assign a signal to the pixel according to the distance, detect a peak of distribution of the signals in the pathological image, and input an image centered on the peak as the learning pattern.

2. The pathological diagnosis support device in accordance with claim 1, wherein the diagnosis means diagnoses the input patterns according a result of the diagnosis and the category table.

3. The pathological diagnosis support device in accordance with claim 1, wherein
   the feature determining means prepares a predetermined number of sets for a transition of the learning pattern according to a value of the feature, calculates the feature of each of the learning patterns, determines the feature candidate, distributes the learning pattern with a weight according to the feature thus determined, sequentially causes a transition of the learning pattern to one of the sets corresponding to the feature, and sequentially determines the feature candidate under a condition that information about the sets respectively containing the learning patterns and the determined feature are known; and
   the diagnosis means causes a transition of each of the input patterns according to each feature of the input patterns and a transition table sequentially having recorded a set to which the learning pattern belongs at determination of each feature of the feature set and diagnoses the input patterns according to a set to which the input pattern belongs as a result of the transition.

4. The pathological diagnosis support device in accordance with claim 1, wherein the feature determining means prepares a predetermined number of sets for a transition of the learning pattern according to a value of the feature, calculates the feature of each of the learning patterns, determines the feature candidate, distributes the learning pattern with a weight according to the feature thus determined, sequentially causes a transition of the learning pattern to one of the sets corresponding to the feature, and sequentially determines the feature candidate under a condition that information about the sets respectively containing the learning patterns and the determined feature are known;

the feature extracting means calculates the feature that indicates a probability with which the feature at an order takes a predetermined value; and the diagnosis means calculates, according to each feature of the input patterns and a transition table sequentially having recorded a set to which the learning pattern belongs at determination of each feature of the feature set, a probability with which the input pattern includes predetermined class information and then conducts the diagnosis.

5. The pathological diagnosis support device in accordance with claim 1, wherein the feature candidates generated by the feature generator means includes a feature candidate obtained using a complex Gabor function as a feature extraction function.

6. The pathological diagnosis support device in accordance with claim 1, wherein the feature candidates generated by the feature generator means includes a feature candidate obtained using a feature extraction function obtained by normalizing a complex Gabor function.

7. A pathological diagnosis support device comprising:

learning pattern input means for obtaining images centered on a tumor from a pathological image and inputting thereto the images as learning patterns;

learning pattern storage means for storing and keeping the learning patterns to which class information is attached;

feature candidate generator means for generating a plurality of feature candidates;

feature determining means for determining a feature set of features suitable for diagnosis using the feature candidates generated by the feature candidate generator means;

feature storage means for storing and keeping the set of features determined by the feature determining means;

category table generator means for generating a category table;

pattern input means for obtaining, from a pathological image to be diagnosed, images centered on a tumor candidate and inputting the images as input patterns;

feature extracting means for extracting features from the input patterns; and diagnosis means for conducting diagnosis using the features, wherein:

the feature determining means calculates a feature of each of the learning patterns corresponding to each of the feature candidates and determines as a first feature of the feature set, a feature candidate for which a mutual information quantity with respect to the class information of a set of the learning patterns takes a maximum value; and sequentially determines, under a condition that the determined feature is known, as a subsequent feature of the feature set, a feature candidate for which mutual information quantity between a feature of each learning pattern corresponding to each feature candidate and the class information of an associated one of the learning patterns takes a maximum value;

the category table generator means calculates each feature of each of the learning patterns using the feature set and classifies the patterns using the category table including each feature of the learning patterns and the class information; and the feature extracting means calculates each feature of the input patterns using the feature set, wherein the feature candidates generated by the feature generator means includes a feature function discriminating a color of the tumor, and wherein the feature determining means compares the signal of each pixel included in the learning patterns calculated by the learning pattern input means with a predetermined threshold value; and wherein the learning pattern input means and the pattern input means select, from R, G, and B values of each pixel in the pathological image stained in advance, pixels belonging to a color region to which a cell nucleus of a predetermined tumor belongs, calculate distance between a center of distribution of the color region and each pixel belonging to the color region, assign a signal to the pixel according to the distance, detect a peak of distribution of the signals in the pathological image, and input an image centered on the peak as the learning pattern.

8. A pathological diagnosis support device comprising:

learning pattern input means for obtaining images centered on a tumor from a pathological image and inputting thereto the images as learning patterns;

learning pattern storage means for storing and keeping the learning patterns to which class information is attached;

feature candidate generator means for generating a plurality of feature candidates;

feature determining means for determining a feature set of features suitable for diagnosis using the feature candidates generated by the feature candidate generator means;

feature storage means for storing and keeping the set of features determined by the feature determining means;

category table generator means for generating a category table;

pattern input means for obtaining, from a pathological image to be diagnosed, images centered on a tumor candidate and inputting the images as input patterns;

feature extracting means for extracting features from the input patterns; and diagnosis means for conducting diagnosis using the features, wherein:

the feature determining means calculates a feature of each of the learning patterns corresponding to each of the feature candidates and determines as a first feature of the feature set, a feature candidate for which a mutual information quantity with respect to the class information of a set of the learning patterns takes a maximum value; and sequentially determines, under a condition that the determined feature is known, as a subsequent feature of the feature set, a feature candidate for which mutual information quantity between a feature of each learning pattern corresponding to each feature candidate and the class information of an associated one of the learning patterns takes a maximum value;

the category table generator means calculates each feature of each of the learning patterns using the feature set and classifies the patterns using the category table including each feature of the learning patterns and the class information; and the feature extracting means calculates each feature of the input patterns using the feature set, wherein the feature candidates generated by the feature generator means includes a feature function discriminating a color of the tumor, and wherein the feature determining means compares the signal of each pixel included in the learning patterns calculated by the learning pattern input means with a mean value of signals of pixels in the proximity of the pixel; and wherein the learning pattern input means and the pattern input means select, from R, G, and B values of each pixel in the pathological image stained in advance, pixels belonging to a color region to which a cell nucleus of a predetermined tumor belongs, calculate distance between a center of distribution of the color region and each pixel belonging to the color region, assign a signal to the pixel according to the distance, detect a peak of distribution of the signals in the pathological image, and input an image centered on the peak as the learning pattern.

9. The pathological diagnosis support device in accordance with claim 5, wherein the feature determining means conducts operation for each of the learning patterns using a predetermined noise parameter for each of the feature candidates.

10. The pathological diagnosis support device in accordance with claim 5, wherein the feature determining means calculates, as the feature of each of the learning patterns corresponding to each of the feature candidates, a probability with which the feature of the learning pattern takes a predetermined value.

11. The pathological diagnosis support device in accordance with claim 1, wherein when the learning patterns can be classified irrespective of the values of the features, the category table generator means substitutes a redundant term for the value of the feature at an associated position of the category table.

12. The pathological diagnosis support device in accordance with claim 1, wherein:

each of the features of the input patterns is a value of a probability with which the feature at an order takes a predetermined value; and the diagnosis means calculates, by use of the features, a probability with which each of the feature patterns contained in the category table takes a predetermined value of class information, the probability being used for decision.

13. A pathological diagnosis support program on computer readable medium for use with a pathological diagnosis support device comprising learning pattern input means for obtaining from a pathological image, images centered on a tumor and inputting thereto the images as learning patterns; learning pattern storage means for storing and keeping the learning patterns to which class information is attached; feature candidate generator means for generating a plurality of feature candidates; feature determining means for determining a feature set of features suitable for diagnosis using the feature candidates generated by the feature candidate generator means; feature storage means for storing and keeping the set of features determined by the feature determining means; category table generator means for generating a category table; pattern input means for obtaining, from a pathological image to be diagnosed, images centered on a tumor candidate and inputting the images as input patterns; feature extracting means for extracting features from the input patterns; and diagnosis means for conducting diagnosis using the features, said program comprising instructions that cause the pathological diagnosis support device to perform steps of:

calculating, using the feature determining means, a feature of each of the learning patterns corresponding to each of the feature candidates and determining as a first feature of the feature set, a feature candidate for which a mutual information quantity with respect to the class information of a set of the learning patterns takes a maximum value, and sequentially determining, under a condition that the determined feature is known, as a subsequent feature of the feature set, a feature candidate for which mutual information quantity between a feature of each learning pattern corresponding to each feature candidate and the class information of an associated one of the learning patterns takes a maximum value;

calculating, using the category table generator means, each feature of each of the learning patterns using the feature set and classifying the patterns using the category table including each feature of the learning patterns and the class information;

calculating, using the feature extracting means, each feature of the input patterns using the feature set;

processing to select, from R, G, and B values of each pixel in the pathological image stained in advance, pixels belonging to a color region to which a cell nucleus of a predetermined tumor belongs;

processing to calculate distance between a center of distribution of the color region and each pixel belonging to the color region;

processing to assign a signal to the pixel according to the distance;

processing to detect a peak of distribution of the signals in the pathological image; and processing to input an image centered on the peak as the learning pattern.

14. The pathological diagnosis support program in accordance with claim 13, wherein the program further executes processing in which the diagnosis means diagnoses the input patterns according a result of the diagnosis and the category table.

15. The pathological diagnosis support program in accordance with claim 13, wherein executed are processing in which the feature determining means prepares a predetermined number of sets for a transition of the learning pattern according to a value of the feature, calculates the feature of each of the learning patterns, determines the feature candidate, distributes the learning pattern with a weight according to the feature thus determined, sequentially causes a transition of the learning pattern to one of the sets corresponding to the feature, and sequentially determines the feature candidate under a condition that information about the sets respectively containing the learning patterns and the determined feature are known; and processing in which the diagnosis means causes a transition of each of the input patterns according to each feature of the input patterns and a transition table sequentially having recorded a set to which the learning pattern belongs at determination of each feature of the feature set and diagnoses the input patterns according a set to which the input pattern belongs as a result of the transition.

16. The pathological diagnosis support program in accordance with claim 13, wherein executed are processing in which the feature determining means prepares a predetermined number of sets for a transition of the learning pattern according to a value of the feature, calculates the feature of each of the learning patterns, determines the feature candidate, distributes the learning pattern with a weight according to the feature thus determined, sequentially causes a transition of the learning pattern to one of the sets corresponding to the feature, and sequentially determines the feature candidate under a condition that information about the sets respectively containing the learning patterns and the determined feature are known;

processing in which the feature extracting means calculates the feature that indicates a probability with which the feature at an order takes a predetermined value; and processing in which the diagnosis means calculates, according to each feature of the input patterns and a transition table sequentially having recorded a set to which the learning pattern belongs at determination of each feature of the feature set, a probability with which the input pattern includes predetermined class information and then conducts the diagnosis.

17. The pathological diagnosis support program in accordance with claim 13, wherein the feature candidates generated by the feature generator means includes a feature candidate obtained using a complex Gabor function as a feature extraction function.

18. The pathological diagnosis support program in accordance with claim 13, wherein the feature candidates generated by the feature generator means includes a feature candidate obtained using a feature extraction function obtained by normalizing a complex Gabor function.

19. A pathological diagnosis support program, on computer readable medium for use with a pathological diagnosis support device comprising learning pattern input means for obtaining from a pathological image, images centered on a tumor and inputting thereto the images as learning patterns; learning pattern storage means for storing and keeping the learning patterns to which class information is attached; feature candidate generator means for generating a plurality of feature candidates; feature determining means for determining a feature set of features suitable for diagnosis using the feature candidates generated by the feature candidate generator means; feature storage means for storing and keeping the set of features determined by the feature determining means; category table generator means for generating a category table; pattern input means for obtaining, from a pathological image to be diagnosed, images centered on a tumor candidate and inputting the images as input patterns; feature extracting means for extracting features from the input patterns; and diagnosis means for conducting diagnosis using the features, said program comprising instructions that cause the pathological diagnosis support device to perform steps of:

calculating, using the feature determining means, a feature of each of the learning patterns corresponding to each of the feature candidates and determining as a first feature of the feature set, a feature candidate for which a mutual information quantity with respect to the class information of a set of the learning patterns takes a maximum value, and sequentially determining, under a condition that the determined feature is known, as a subsequent feature of the feature set, a feature candidate for which mutual information quantity between a feature of each learning pattern corresponding to each feature candidate and the class information of an associated one of the learning patterns takes a maximum value;

calculating, using the category table generator means, each feature of each of the learning patterns using the feature set and classifying the patterns using the category table including each feature of the learning patterns and the class information;

calculating, using the feature extracting means, each feature of the input patterns using the feature set;

comparing, using the feature determining means, the signal of each pixel included in the learning patterns calculated by the learning pattern input means with a predetermined threshold value;

selecting, from R, G, and B values of each pixel in the pathological image stained in advance, pixels belonging to a color region to which a cell nucleus of a predetermined tumor belongs;

calculating distance between a center of distribution of the color region and each pixel belonging to the color region;

assigning a signal to the pixel according to the distance;

detecting a peak of distribution of the signals in the pathological image; and inputting an image centered on the peak as the learning pattern, wherein the feature candidates generated by the feature generator means includes a feature function discriminating a color of the tumor.

20. A pathological diagnosis support program on computer readable medium for use with a pathological diagnosis support device comprising learning pattern input means for obtaining from a pathological image, images centered on a tumor and inputting thereto the images as learning patterns; learning pattern storage means for storing and keeping the learning patterns to which class information is attached; feature candidate generator means for generating a plurality of feature candidates; feature determining means for determining a feature set of features suitable for diagnosis using the feature candidates generated by the feature candidate generator means; feature storage means for storing and keeping the set of features determined by the feature determining means; category table generator means for generating a category table; pattern input means for obtaining, from a pathological image to be diagnosed, images centered on a tumor candidate and inputting the images as input patterns; feature extracting means for extracting features from the input patterns; and diagnosis means for conducting diagnosis using the features, said program comprising instructions that cause the pathological diagnosis support device to perform steps of:

calculating, using the feature determining means, a feature of each of the learning patterns corresponding to each of the feature candidates and determining as a first feature of the feature set, a feature candidate for which a mutual information quantity with respect to the class information of a set of the learning patterns takes a maximum value, and sequentially determining, under a condition that the determined feature is known, as a subsequent feature of the feature set, a feature candidate for which mutual information quantity between a feature of each learning pattern corresponding to each feature candidate and the class information of an associated one of the learning patterns takes a maximum value;

calculating, using the category table generator means, each feature of each of the learning patterns using the feature set and classifying the patterns using the category table including each feature of the learning patterns and the class information;

calculating, using the feature extracting means, each feature of the input patterns using the feature set;

comparing, using the feature determining means, the signal of each pixel included in the learning patterns calculated by the learning pattern input means with a mean value of signals of pixels in the proximity of the pixel;

selecting, from R, G, and B values of each pixel in the pathological image stained in advance, pixels belonging to a color region to which a cell nucleus of a predetermined tumor belong;

calculating distance between a center of distribution of the color region and each pixel belonging to the color region;

assigning a signal to the pixel according to the distance;

detecting a peak of distribution of the signals in the pathological image; and inputting an image centered on the peak as the learning pattern, wherein the feature candidates generated by the feature generating means includes a feature function discriminating a color of the tumor.

21. The pathological diagnosis support program in accordance with claim 17, further comprising processing in which the feature determining means conducts operation for each of the learning patterns using a predetermined noise parameter for each of the feature candidates.

22. The pathological diagnosis support program in accordance with claim 17, further comprising processing in which the feature determining means calculates, as the feature of each of the learning patterns corresponding to each of the feature candidates, a probability with which the feature of the learning pattern takes a predetermined value.

23. The pathological diagnosis support program in accordance with claim 13, further comprising processing in which when the learning patterns can be classified irrespectively of the values of the features, the category table generator means substitutes a redundant term for the value of the feature at an associated position of the category table.

24. The pathological diagnosis support program in accordance with claim 13, wherein:
each of the features of the input patterns is a value of a probability with which the feature at an order takes a predetermined value, the program further comprising processing in which the diagnosis means calculates, by use of the features, a probability with which each of the feature patterns contained in the category table takes a predetermined value of class information, the probability being used for decision.

25. A pathological diagnosis support method for use with a pathological diagnosis support device comprising learning pattern input means for obtaining from a pathological image to be used for learning, images centered on a tumor and inputting thereto the images as learning patterns; learning pattern storage means for storing and keeping the learning patterns to which class information is attached; feature candidate generator means for generating a plurality of feature candidates; feature determining means for determining a feature set of features suitable for diagnosis using the feature candidates generated by the feature candidate generator means; feature storage means for storing and keeping the set of features determined by the feature determining means; category table generator means for generating a category table; pattern input means for obtaining, from a pathological image to be diagnosed, images centered on a tumor candidate and inputting the images as input patterns; feature extracting means for extracting features from the input patterns; and diagnosis means for conducting diagnosis using the features, the method comprising: using a processors to perform steps of a first step in which the feature determining means calculates a feature of each of the learning patterns corresponding to each of the feature candidates and determines as a first feature of the feature set, a feature candidate for which a mutual information quantity with respect to the class information of a set of the learning patterns takes a maximum value; and sequentially determines, under a condition that the determined feature is known, as a subsequent feature of the feature set, a feature candidate for which mutual information quantity between a feature of each learning pattern corresponding to each feature candidate and the class information of an associated one of the learning patterns takes a maximum value;

a second step in which the category table generator means calculates each feature of each of the learning patterns using the feature set and classifies the patterns using the category table including each feature of the learning patterns and the class information;

a third step in which the feature extracting means calculates each feature of the input patterns using the feature set; and steps to be executed by the learning pattern input means and the pattern input means, the steps including:

a step of selecting, from R, G, and B values of each pixel in the pathological image stained in advance, pixels belonging to a color region to which a cell nucleus of a predetermined tumor belongs;

a step of calculating distance between a center of distribution of the color region and each pixel belonging to the color region;

a step of assigning a signal to the pixel according to the distance;

a step of detecting a peak of distribution of the signals in the pathological image; and a step of inputting an image centered on the peak as the learning pattern.

26. The pathological diagnosis support method in accordance with claim 25, wherein the method further comprises a fourth step in which the diagnosis means diagnoses the input patterns according a result of the diagnosis and the category table.

27. The pathological diagnosis support method in accordance with claim 25 wherein in the first step the feature determining means prepares a predetermined number of sets for a transition of the learning pattern according to a value of the feature, calculates the feature of each of the learning patterns, determines the feature candidate, distributes the learning pattern with a weight according to the feature thus determined, sequentially causes a transition of the learning pattern to one of the sets corresponding to the feature, and sequentially determines the feature candidate under a condition that information about the sets respectively containing the learning patterns and the determined feature are known, the method further comprising a fourth step in which the diagnosis means causes a transition of each of the input patterns according to each feature of the input patterns and a transition table sequentially having recorded a set to which the learning pattern belongs at determination of each feature of the feature set and diagnoses the input patterns according a set to which the input pattern belongs as a result of the transition.

28. The pathological diagnosis support method in accordance with claim 25, wherein
in the first step the feature determining means prepares a predetermined number of sets for a transition of the learning pattern according to a value of the feature, calculates the feature of each of the learning patterns, determines the feature candidate, distributes the learning pattern with a weight according to the feature thus determined, sequentially causes a transition of the learning pattern to one of the sets corresponding to the feature, and sequentially determines the feature candidate under a condition that information about the sets respectively containing the learning patterns and the determined feature are known, and
in the third step the feature extracting means calculates the feature that indicates a probability with which the feature at an order takes a predetermined value, the method further comprising
a fourth step in which the diagnosis means calculates, according to each feature of the input patterns and a transition table sequentially having recorded a set to which the learning pattern belongs at determination of each feature of the feature set, a probability with which the input pattern includes predetermined class information and then conducts the diagnosis.

29. The pathological diagnosis support method in accordance with claim 25, wherein the feature candidates generated by the feature generator means includes a feature candidate obtained using a complex (labor function as a feature extraction function.

30. The pathological diagnosis support method in accordance with claim 25, wherein the feature candidates generated by the feature generator means includes a feature candidate obtained using a feature extraction function obtained by normalizing a complex Gabor function.

31. A pathological diagnosis support method comprising learning pattern input means for obtaining from a pathological image to be used for learning, images centered on a tumor and inputting thereto the images as learning patterns; learning pattern storage means for storing and keeping the learning patterns to which class information is attached; feature candidate generator means for generating a plurality of feature candidates; feature determining means for determining a feature set of features suitable for diagnosis using the feature candidates generated by the feature candidate generator means; feature storage means for storing and keeping the set of features determined by the feature determining means; category table generator means for generating a category table; pattern input means for obtaining, from a pathological image to be diagnosed, images centered on a tumor candidate and inputting the images as input patterns; feature extracting means for extracting features from the input patterns; and diagnosis means for conducting diagnosis using the features, the method comprising: using a processors to perform steps of
a first step in which the feature determining means calculates a feature of each of the learning patterns corresponding to each of the feature candidates and determines as a first feature of the feature set, a feature candidate for which a mutual information quantity with respect to the class information of a set of the learning patterns takes a maximum value; and sequentially determines, under a condition that the determined feature is known, as a subsequent feature of the feature set, a feature candidate for which mutual information quantity between a feature of each learning pattern corresponding to each feature candidate and the class information of an associated one of the learning patterns takes a maximum value;
a second step in which the category table generator means calculates each feature of each of the learning patterns using the feature set and classifies the patterns using the category table including each feature of the learning patterns and the class information;
a third step in which the feature extra6ting means calculates each feature of the input patterns using the feature set;
a fourth step in which the feature determining means compares the signal of each pixel included in the learning patterns calculated by the learning pattern input means with a predetermined threshold value;
a step of selecting from R, G, and B values of each pixel in the pathological image stained in advance, pixels belonging to a color region to which a cell nucleus of a predetermined tumor belongs;
a step of calculating distance between a center of distribution of the color region and each pixel belonging to the color region;
a step of assigning a signal to the pixel according to the distance;
a step of detecting a peak of distribution of the signals in the pathological image; and
a step of inputting an image centered on the peak as the learning pattern,
wherein the feature candidates generated by the feature generator means includes a feature function discriminating a color of the tumor.

32. A pathological diagnosis support method, comprising learning pattern input means for obtaining from a pathological image to be used for learning, images centered on a tumor and inputting thereto the images as learning patterns; learning pattern storage means for storing and keeping the learning patterns to which class information is attached; feature candidate generator means for generating a plurality of feature candidates; feature determining means for determining a feature set of features suitable for diagnosis using the feature candidates generated by the feature candidate generator means; feature storage means for storing and keeping the set of features determined by the feature determining means; category table generator means for generating a category table; pattern input means for obtaining, from a pathological image to be diagnosed, images centered on a tumor candidate and inputting the images as input patterns; feature extracting means for extracting features from the input patterns; and diagnosis means for conducting diagnosis using the features, the method comprising: using a processors to perform steps of
a first step in which the feature determining means calculates a feature of each of the learning patterns corresponding to each of the feature candidates and determines as a first feature of the feature set, a feature candidate for which a mutual information quantity with respect to the class information of a set of the learning patterns takes a maximum value; and sequentially determines, under a condition that the determined feature is known, as a subsequent feature of the feature set, a feature candidate for which mutual information quantity between a feature of each learning pattern corresponding to each feature candidate and the class information of an associated one of the learning patterns takes a maximum value;

a second step in which the category table generator means calculates each feature of each of the learning patterns using the feature set and classifies the patterns using the category table including each feature of the learning patterns and the class information;

a third step in which the feature extracting means calculates each feature of the input patterns using the feature set;

a fourth step in which the feature determining means compares the signal of each pixel included in the learning patterns calculated by the learning pattern input means with a mean value of signals of pixels in the proximity of the pixel;

a step of selecting, from R, G, and B values of each pixel in the pathological image stained in advance, pixels belonging to a color region to which a cell nucleus of a predetermined tumor belongs;

a step of calculating distance between a center of distribution of the color region and each pixel belonging to the color region;

a step of assigning a signal to the pixel according to the distance;

a step of detecting a peak of distribution of the signals in the pathological image; and a step of inputting an image centered on the peak as the learning pattern, wherein the feature candidates generated by the feature generator means includes a feature function discriminating a color of the tumor.

33. The pathological diagnosis support method in accordance with claim 29, further comprising a step in which the feature determining means conducts operation for each of the learning patterns using a predetermined noise parameter for each of the feature candidates.

34. The pathological diagnosis support method in accordance with claim 29, further comprising a step in which the feature determining means calculates, as the feature of each of the learning patterns corresponding to each of the feature candidates, a probability with which the feature of the learning pattern takes a predetermined value.

35. The pathological diagnosis support method in accordance with claim 25, further comprising a step in which when the learning patterns can be classified irrespectively of the values of the features, the category table generator means substitutes a redundant term for the value of the feature at an associated position of the category table.

36. The pathological diagnosis support method in accordance with claim 25, wherein:

each of the features of the input patterns is a value of a probability with which the feature at an order takes a predetermined value, the method further comprising a step in which the diagnosis means calculates, by use of the features, a probability with which each of the feature patterns contained in the category table takes a predetermined value of class information, the probability being used for decision.

37. A pathological diagnosis support system, comprising:

an information processing terminal for keeping pathological image data including a pathological image and information unique to a patient attached to the image; and a pathological diagnosis server for diagnosing the pathological image data, the server comprising:

a pathological diagnosis support device according to one of claims 1 to 4, 6 to 8, 10 to 14 for diagnosing the pathological image contained in the pathological image data; and diagnosis result storage means for storing a diagnosis result from the pathological diagnosis support device together with the information unique to the patient, wherein the information processing terminal requests the pathological diagnosis server to transmit to the terminal the diagnosis result together with the information unique to the patient, and the pathological diagnosis server compares the information unique to the patient received from the terminal with the information unique to the patient stored together with the diagnosis result and then transmits the diagnosis result to the terminal if the information unique to the patient received from the terminal matches the information unique to the patient stored together with the diagnosis result.

38. The pathological diagnosis support system in accordance with claim 37, further comprising an accounting server for keeping amounts of use charge respectively of the pathological diagnosis support device and the information processing terminal.

39. The pathological diagnosis support system in accordance with claim 38, wherein when the diagnosis result storage means stores the diagnosis result, the accounting server accumulates an amount of use charge of the pathological diagnosis support system.

40. The pathological diagnosis support system in accordance with claim 38, wherein when the information processing terminal receives the diagnosis result, the accounting server accumulates an amount of use charge of the information processing terminal.

* * * * *